United States Patent
Kelly et al.

(10) Patent No.: US 11,534,614 B2
(45) Date of Patent: *Dec. 27, 2022

(54) MANAGING RECHARGE POWER FOR IMPLANTABLE MEDICAL DEVICES

(71) Applicant: Medtronic, Inc., Minneapolis, MN (US)

(72) Inventors: Kevin J. Kelly, Shoreview, MN (US); David P. Olson, Minnetrista, MN (US); Reid K. Bornhoft, Lino Lakes, MN (US); Venkat R. Gaddam, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 220 days.

This patent is subject to a terminal disclaimer.

(21) Appl. No.: 16/879,159

(22) Filed: May 20, 2020

(65) Prior Publication Data

US 2020/0276446 A1 Sep. 3, 2020

Related U.S. Application Data

(63) Continuation of application No. 13/360,443, filed on Jan. 27, 2012, now Pat. No. 10,682,520.

(51) Int. Cl.
*A61N 1/378* (2006.01)

(52) U.S. Cl.
CPC ...... *A61N 1/3787* (2013.01); *F04C 2270/041* (2013.01)

(58) Field of Classification Search
CPC ........ A61N 1/08; A61N 1/3603–36034; A61N 1/36128–36139; A61N 1/36142; A61N 1/37–3704; A61N 1/37276; A61N 1/3787; A61N 1/3925–3943
See application file for complete search history.

(56) References Cited

U.S. PATENT DOCUMENTS

| | | |
|---|---|---|
| 5,702,431 A | 12/1997 | Wang et al. |
| 6,099,494 A | 8/2000 | Henniges et al. |
| 6,185,456 B1 | 2/2001 | Garrett |

(Continued)

FOREIGN PATENT DOCUMENTS

CN 101516442 A 8/2009

OTHER PUBLICATIONS

Patent Examination Report No. 1 from counterpart Australian Patent Application No. 2012367269, dated Sep. 19, 2014, 3 pp.

(Continued)

*Primary Examiner* — Thaddeus B Cox
(74) *Attorney, Agent, or Firm* — Shumaker & Sieffert, P.A.

(57) ABSTRACT

Devices, systems, and techniques for controlling charging power based on a cumulative thermal dose to a patient are disclosed. Implantable medical devices may include a rechargeable power source that can be transcutaneously charged. An external charging device may calculate an estimated cumulative thermal dose delivered to the patient during charging over a predetermined period of time. Based on the estimated cumulative thermal dose, the external charging device may select a power level for subsequent charging of the rechargeable power source. In one example, the charging device may select a high power level when the cumulative thermal dose has not exceeded a thermal dose threshold and select a low power level when the cumulative thermal dose has exceeded the thermal dose threshold.

20 Claims, 10 Drawing Sheets

(56) References Cited

U.S. PATENT DOCUMENTS

| | | | |
|---|---|---|---|
| 6,227,204 | B1 | 5/2001 | Baumann et al. |
| 6,313,612 | B1 | 11/2001 | Honda et al. |
| 6,664,763 | B2 | 12/2003 | Echarri et al. |
| 6,878,481 | B2 | 4/2005 | Bushong et al. |
| 7,093,601 | B2 | 8/2006 | Manker et al. |
| 7,339,353 | B1 | 3/2008 | Masias et al. |
| 7,582,387 | B2 | 9/2009 | Howard et al. |
| 7,635,541 | B2 | 12/2009 | Scott et al. |
| 7,734,353 | B2 | 6/2010 | Gerber et al. |
| 7,819,826 | B2 | 10/2010 | Diederich et al. |
| 7,907,901 | B1 | 3/2011 | Kahn et al. |
| 8,134,256 | B2 | 3/2012 | Onishi et al. |
| 8,169,185 | B2 | 5/2012 | Partovi et al. |
| 8,278,871 | B2 | 10/2012 | Kallmyer |
| 8,482,250 | B2 | 7/2013 | Soar |
| 8,509,912 | B2 | 8/2013 | Morgan et al. |
| 8,620,484 | B2 | 12/2013 | Baarman et al. |
| 9,042,995 | B2 | 5/2015 | Dinsmoor et al. |
| 9,270,134 | B2 | 2/2016 | Gaddam et al. |
| 10,682,520 | B2 | 6/2020 | Kelly et al. |
| 2004/0234865 | A1 | 11/2004 | Sato et al. |
| 2007/0188323 | A1 | 8/2007 | Sinclair et al. |
| 2007/0270921 | A1 | 11/2007 | Strother et al. |
| 2008/0019514 | A1 | 1/2008 | Stromberg et al. |
| 2008/0183165 | A1 | 7/2008 | Buysse et al. |
| 2009/0005770 | A1 | 1/2009 | Gerber et al. |
| 2009/0088623 | A1 | 4/2009 | Vortman et al. |
| 2009/0112291 | A1 | 4/2009 | Wahlstrand et al. |
| 2009/0276014 | A1 | 11/2009 | Morgan et al. |
| 2010/0010582 | A1 | 1/2010 | Carbunaru et al. |
| 2010/0047671 | A1 | 2/2010 | Chiang et al. |
| 2010/0137948 | A1 | 6/2010 | Aghassian et al. |
| 2010/0199092 | A1 | 8/2010 | Andrus et al. |
| 2010/0256709 | A1 | 10/2010 | Kallmyer |
| 2010/0301803 | A1 | 12/2010 | Flemming |
| 2010/0305662 | A1 | 12/2010 | Ozawa et al. |
| 2011/0071597 | A1 | 3/2011 | Aghassian |
| 2011/0087307 | A1 | 4/2011 | Carbunaru et al. |
| 2012/0262108 | A1 | 10/2012 | Olson et al. |
| 2013/0197613 | A1 | 8/2013 | Kelly et al. |

OTHER PUBLICATIONS

First Office Action, and translation thereof, from counterpart Chinese Application No. 201280068161.3, dated Jun. 2, 2015, 17 pp.
Response to Office Action dated Apr. 23, 2015 from U.S. Appl. No. 13/749,481, filed Jul. 23, 2015, 16 pp.
Second Office Action and Search Report, and translation thereof, from counterpart Chinese Application No. 201280068161.3, dated Feb. 16, 2016, 25 pp.
International Search Report and Written Opinion of international application No. PCT/US2012/069124, dated Apr. 5, 2013, 9 pp.
U.S. Appl. No. 61/591,716, filed Jan. 27, 2012, entitled, "Adaptive Rate Recharging System."
U.S. Appl. No. 13/360,520, filed Jan. 27, 2012, entitled "Battery Charging Top-Off."
U.S. Appl. No. 13/360,531, filed Jan. 27, 2012, entitled "Battery Charging Top-Off."
U.S. Appl. No. 12/699,830, filed Feb. 3, 2010, entitled "Implantable Medical Devices and Systems Having Power Management for Recharge Sessions."
Patent Examination Report No. 2, from counterpart Australian Patent Application No. 2012367269, dated May 21, 2015, 4 pp.
Notice of Acceptance from counterpart Australian Patent Application No. 2012367269, dated Jul. 6, 2015, 50 pp.
Response to Second Examination report dated May 21, 2015, from counterpart Australian Patent Application No. 2012367269, filed on Jun. 22, 2015, 11 pp.
Request to Amend Complete Specification from counterpart Australian Patent Application No. 2012367269, filed an Mar. 26, 2015, 22 pp.
Preliminary Amendment filed in counterpart European Patent Application No. 12788690.1, filed on May 23, 2014, 4 pp.
Argument and Claims, and translation thereof, from counterpart Chinese Patent Application No. 201280068161.3, filed Jan. 16, 2017, 10 pp.
Argument and Claims, and translation thereof, from counterpart Chinese Patent Application No. 201280068161.3, filed Jul. 4, 2016, 29 pp.
Response to Communication under Rule 161(1) EPC from counterpart European Application No. 12816389.6, filed on May 6, 2015, 7 pp.
Written Argument, and translation thereof, from counterpart Japanese Patent Application No. 2014-554718, filed on Aug. 23, 2016, 31 pp.
International Preliminary Report on Patentability from International Application No. PCT/US2012/069124, dated Jul. 29, 2014, 5 pp.
Prosecution History from U.S. Appl. No. 13/360,443, dated Nov. 22, 2013 through Feb. 5, 2020.
Prosecution History from U.S. Appl. No. 13/749,481, dated Apr. 23, 2015 through Oct. 15, 2015.
Notification of Grant, and translation thereof, from counterpart Chinese Patent Application No. 201280068161.3, dated Mar. 30, 2017, 3 pp.

US 11,534,614 B2

MANAGING RECHARGE POWER FOR IMPLANTABLE MEDICAL DEVICES

This application is a continuation of U.S. patent application Ser. No. 13/360,443, filed Jan. 27, 2012, now U.S. Pat. No. 10,682,520 the entire content of which is incorporated herein by reference.

TECHNICAL FIELD

The disclosure relates to implantable medical devices and, more particularly, rechargeable power supplies for implantable medical devices.

BACKGROUND

Implantable medical devices may be used to monitor a patient condition and/or deliver therapy to the patient. In long term or chronic uses, implantable medical devices may include a rechargeable power source (e.g., comprising one or more capacitors or batteries) that extends the operational life of the medical device to weeks, months, or even years over a non-rechargeable device.

When the energy stored in the rechargeable power source has been depleted, the patient may use an external charging device to recharge the power source. Since the rechargeable power source is implanted in the patient and the charging device is external of the patient, this charging process may be referred to as transcutaneous charging. In some examples, transcutaneous charging may be performed via inductive coupling between a primary coil in the charging device and a secondary coil in the implantable medical device. When a current is applied to the primary coil and the primary coil is aligned to the secondary coil, electrical current is induced in the secondary coil within the patient. Therefore, the external charging device does not need to physically connect with the rechargeable power source for charging to occur.

SUMMARY

In general, the disclosure is directed to devices, systems, and techniques for controlling charging power based on an estimation of a cumulative thermal dose delivered to a patient during a charging period. An external charging device may be used to transcutaneously charge a rechargeable power source of the IMD. An external charging device may calculate an estimated cumulative thermal dose delivered to the patient during the charging process. Based on the calculated cumulative thermal dose, the external charging device may control charging of the rechargeable power source. For example, the external charging device may select a power level for subsequent charging of the rechargeable power source.

In one aspect, the disclosure is directed to a method that includes calculating, by a processor, an estimated cumulative thermal dose delivered to a patient during charging of a rechargeable power source of an implantable medical device over a period of time and selecting, by the processor, a power level for subsequent charging of the rechargeable power source based on the estimated calculated cumulative thermal dose.

In another aspect, the disclosure is directed to a device that includes a processor configured to calculate an estimated cumulative thermal dose delivered to a patient during charging of a rechargeable power source of an implantable medical device over a period of time and select a power level for subsequent charging of the rechargeable power source based on the estimated cumulative thermal dose.

In a further aspect, the disclosure is directed to a computer-readable storage medium including instructions that cause at least one processor to calculate an estimated cumulative thermal dose delivered to a patient during charging of a rechargeable power source of an implantable medical device over a period of time and select a power level for subsequent charging of the rechargeable power source based on the estimated cumulative thermal dose.

In another further aspect, the disclosure is directed to a system that includes an implantable medical device comprising a rechargeable power source, an external charging device comprising a charging module configured to charge the rechargeable power source, and at least one processor configured to calculate an estimated cumulative thermal dose delivered to a patient during charging of the rechargeable power source over a period of time and select a power level for subsequent charging of the rechargeable power source based on the estimated cumulative thermal dose.

The details of one or more example are set forth in the accompanying drawings and the description below. Other features, objects, and advantages will be apparent from the description and drawings, and from the claims.

DETAILED DESCRIPTION

Figure 1:
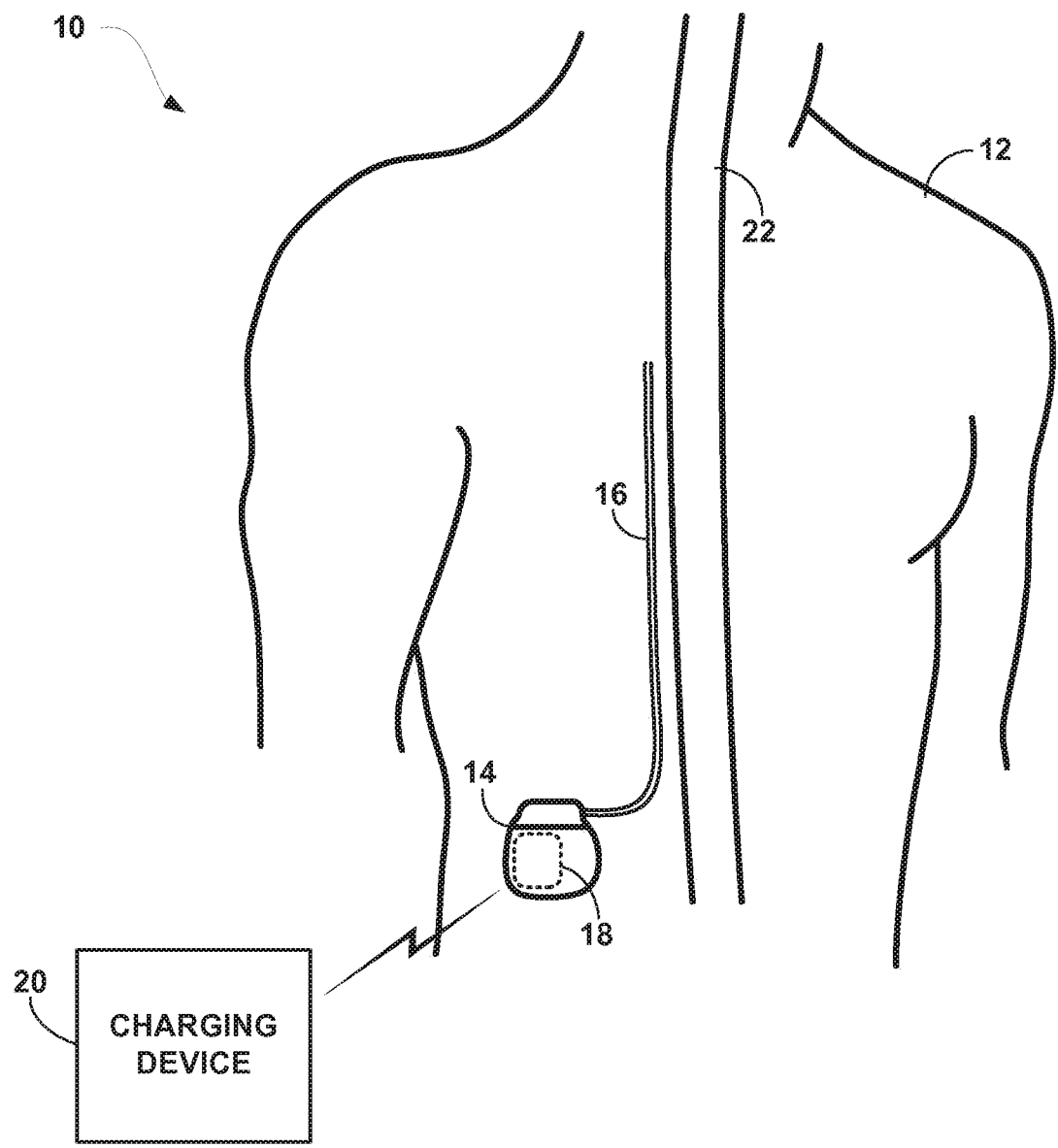
FIG. 1 is a conceptual diagram illustrating an example system that includes an implantable medical device (IMD) and an external charging device that charges a rechargeable power source of the IMD.

This disclosure is generally directed to devices, systems, and techniques for controlling power user to charge a rechargeable power source based on a cumulative thermal dose delivered to a patient. Implantable medical devices (IMDs) may be implanted within a patient and used to monitor a parameter of the patient and/or deliver a therapy to the patient. To extend the operational life of the IMD, the IMD may include a rechargeable power source (e.g., one or more capacitors or batteries). When the rechargeable power source is being recharged, the power transmitted to the IMD may generate heat that increases the temperature of the IMD. In order to prevent this increased temperature from damaging patient tissue adjacent to the IMD, charging sessions may be limited to predetermined durations and/or reduced power levels may be used to recharge the rechargeable power source. However, this approach may increase recharge durations and/or prevent the rechargeable power source from being fully charged.

As disclosed herein, an estimate of the cumulative thermal dose (e.g., an estimated cumulative thermal dose) delivered to the patient during recharging may be calculated on a continual basis. The external charge device may monitor the cumulative thermal dose and control the charging power level of the charging process to limit the heat generated in the 1 MB. For example, the charging device may select a high power level to charge the rechargeable power source at a high rate until the calculated cumulative thermal dose indicates the power level needs to be reduced. The charging device may then terminate charging or select a lower power level to continue charging the rechargeable power source at lower IMD temperatures.

The cumulative thermal dose feedback may thus reduce the need to conservatively estimate recharge times and recharge power levels to keep the temperature of the IMD within safe limits. Instead, the charge device may charge the rechargeable power source at high rates until the cumulative thermal dose indicates that the temperature, and the charge power level, needs to be reduced. Lower power levels may be used to continue charging the rechargeable power source until the power source is fully charged. This closed loop feedback approach may reduce the amount of time needed to charge rechargeable power sources and/or increase the likelihood that the rechargeable power source is fully charged after a recharge session.

The cumulative thermal dose may be an indication, or estimation, of the total amount of heat to which the tissue surrounding the 1 MB has been exposed. Even at temperatures too low to cause immediate tissue necrosis, elevated temperatures may still be undesirable for the patient. Therefore, it may be useful to monitor the amount of time that tissue is exposed to elevated temperatures (e.g., temperatures above 39 degrees Celsius and below 43 degrees Celsius). This cumulative thermal dose may be used to control the recharge process and uncomfortable and undesirable elevated temperatures. For example, the cumulative thermal dose may be calculated by integrating the tissue temperature over a predetermined period of time. Since the exact thermal dose delivered to the patient may be difficult to exactly measure, the cumulative thermal dose described herein may be used as an estimation of the actual cumulative thermal dose delivered to the patient. However, the calculated cumulative thermal dose described herein may be substantially similar to the actual thermal dose received by the patient. The power level used to charge the rechargeable power source may then be selected based on the comparison of the cumulative thermal dose to one or more thresholds.

In some examples, the charging device may select power levels with decreasing intensity as the cumulative thermal dose reaches a threshold. Incrementally decreasing the power level may minimize the risk of exceeding the cumulative thermal dose threshold from residual heat in the IMD even after reducing the power level. In other examples, the charging device may employ a lockout period to prevent frequent use of high power levels during charging. For example, the lockout period may begin after a high power level has ceased, and a new high power level may not be used for charging until after the lockout period has expired. The lockout period may be a predetermined duration of time or determined based on the length of time the previous high power level was used to charge the rechargeable power source.

FIG. 1 is a conceptual diagram illustrating an example system 10 that includes an implantable medical device (IMD) 14 and an external charging device 20 that charges a rechargeable power source 18. Although the techniques described in this disclosure are generally applicable to a variety of medical devices including medical devices such as patient monitors, electrical stimulators, or drug delivery devices, application of such techniques to implantable neurostimualtors will be described for purposes of illustration. More particularly, the disclosure will refer to an implantable neurostimulation system for use in spinal cord stimulation therapy, but without limitation as to other types of medical devices.

As shown in FIG. 1, system 10 includes an IMD 14 and external charging device 20 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. Generally IMD 14 may be a chronic electrical stimulator that remains implanted within patient 12 for weeks, months, or even years. In the example of FIG. 1, IMD 14 and lead 16 may be directed to delivering spinal cord stimulation therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or other internal location. IMD 14 includes rechargeable power source 18 and IMD 14 is coupled to lead 16.

Electrical stimulation energy, which may be constant current or constant voltage based pulses, for example, is delivered from IMD 14 to one or more targeted locations within patient 12 via one or more electrodes (not shown) of lead 16. The parameters for a program that controls delivery of stimulation energy by IMD 14 may include information identifying which electrodes have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes. Electrical stimulation may be delivered in the form of stimulation pulses or continuous waveforms, for example.

In the example of FIG. 1, lead 16 is disposed within patient 12, e.g., implanted within patient 12. Lead 16 tunnels through tissue of patient 12 from along spinal cord 22 to a subcutaneous tissue pocket or other internal location where IMD 14 is disposed. Although lead 16 may be a single lead, lead 16 may include a lead extension or other segments that may aid in implantation or positioning of lead 16. In addition, a proximal end of lead 16 may include a connector (not shown) that electrically couples to a header of IMD 14. Although only one lead 16 is shown in FIG. 1, system 10 may include two or more leads, each coupled to IMD 14 and directed to similar or different target tissue sites. For example, multiple leads may be disposed along spinal cord 22 or leads may be directed to spinal cord 22 and/or other locations within patient 12.

Lead 16 may carry one or more electrodes that are placed adjacent to the target tissue, e.g., spinal cord 22 for spinal cord stimulation (SCS) therapy. One or more electrodes may be disposed at a distal tip of lead 16 and/or at other positions at intermediate points along lead 16, for example. Electrodes of lead 16 transfer electrical stimulation generated by an electrical stimulation generator in IMD 14 to tissue of patient 12. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for therapy. In general, ring electrodes arranged at different axial positions at the distal ends of lead 16 will be described for purposes of illustration.

In alternative examples, lead 16 may be configured to deliver stimulation energy generated by IMD 14 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 16 and IMD 14 may also be configured to provide other types of electrical stimulation or drug therapy (e.g., with lead 16 configured as a catheter). For example, lead 16 may be configured to provide deep brain stimulation (DBS), peripheral nerve stimulation (PNS), or other deep tissue or superficial types of electrical stimulation. In other examples, lead 16 may provide one or more sensors configured to allow IMD 14 to monitor one or more parameters of patient 12. The one or more sensors may be provided in addition to, or in place of, therapy delivery by lead 16.

IMD 14 delivers electrical stimulation therapy to patient 12 via selected combinations of electrodes carried by lead 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 16 is tissue proximate spinal cord 22 (e.g., one or more target locations of the dorsal columns or one or more dorsal roots that branch from spinal cord 22. Lead 16 may be introduced into spinal cord 22 via any suitable region, such as the thoracic, cervical or lumbar regions. Stimulation of dorsal columns, dorsal roots, and/or peripheral nerves may, for example, prevent pain signals from traveling through spinal cord 22 and to the brain of the patient. Patient 12 may perceive the interruption of pain signals as a reduction in pain and, therefore, efficacious therapy results. For treatment of other disorders, lead 16 may be introduced at any exterior location of patient 12. In this manner, skin opening 18 may be located at any exterior skin location in other examples.

Although lead 16 is described as generally delivering or transmitting electrical stimulation signals, lead 16 may additionally or alternatively transmit electrical signals from patient 12 to IMD 14 for monitoring. For example, IMD 14 may utilize detected nerve impulses to diagnose the condition of patient 12 or adjust the delivered stimulation therapy. Lead 16 may thus transmit electrical signals to and from patient 12.

A user, such as a clinician or patient 12, may interact with a user interface of an external programmer (not shown) to program IMD 14. Programming of IMD 14 may refer generally to the generation and transfer of commands, programs, or other information to control the operation of IMD 14. For example, the external programmer may transmit programs, parameter adjustments, program selections, group selections, or other information to control the operation of IMD 14, e.g., by wireless telemetry or wired connection.

In some cases, an external programmer may be characterized as a physician or clinician programmer if it is primarily intended for use by a physician or clinician. In other cases, the external programmer may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use. In other examples, external charging device 20 may be included, or part of, an external programmer. In this manner, a user may program and charge IMD 14 using one device, or multiple devices.

IMD 14 may be constructed of any polymer, metal, or composite material sufficient to house the components of IMD 14 (e.g., components illustrated in FIG. 2) within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, or buttocks. The housing of IMD 14 may be configured to provide a hermetic seal for components, such as rechargeable power source 18. In addition, the housing of IMD 14 may be selected of a material that facilitates receiving energy to charge rechargeable power source 18.

As described herein, rechargeable power source 18 may be included within IMD 14. However, in other examples, rechargeable power source 18 could be located external to a housing of IMD 14, separately protected from fluids of patient 12, and electrically coupled to electrical components of IMD 14. This type of configuration of IMD 14 and rechargeable power source 18 may provide implant location flexibility when anatomical space for implantable devices is minimal. In any case, rechargeable power source 18 may provide operational electrical power to one or more components of IMD 14.

Rechargeable power source 18 may include one or more capacitors, batteries, or components (e.g. chemical or electrical energy storage devices). Example batteries may include lithium-based batteries, nickel metal-hydride batteries, or other materials. Rechargeable power source 18 is also rechargeable. In other words, rechargeable power source 18 may be replenished, refilled, or otherwise capable of increasing the amount of energy stored after energy has been depleted. Rechargeable power source 18 may be subjected to numerous discharge and recharge cycles (e.g., hundreds or even thousands of cycles) over the life of rechargeable power source 18 in IMD 14. Rechargeable power source 18 may be recharged when fully depleted or partially depleted.

Charging device 20 may be used to recharge rechargeable power source 18 and IMD 14 when implanted in patient 12. Charging device 20 may be a hand-held device, a portable device, or a stationary charging system. In any case, charging device 20 may include components necessary to charge rechargeable power source 18 through tissue of patient 12. In some examples, charging device 20 may only perform charging of rechargeable power source 18. In other examples, charging device 20 may be an external programmer or other devices configured to perform additional functions. For example, when embodied as an external programmer, charging device 20 may transmit programming commands to IMD 14 in addition to charge rechargeable power source 18. In another example, charging device 20 may communicate with IMD 14 to transmit and/or receive information related to the charging of rechargeable power source 18. For example, IMD 14 may transmit temperature information of IMD 14 and/or rechargeable power source 18, received power during charging, the charge level of rechargeable power source 18, charge depletion rates during use, or any other information related to power consumption and recharging of IMD 14 and rechargeable power source 18.

Charging device 20 and IMD 14 may utilize any wireless power transfer techniques that are capable of recharging rechargeable power source 18 of IMD 14 when IMD 14 is implanted within patient 14. In one example, system 10 may utilize inductive coupling between a coil of charging device 20 and a coil of IMD 14 coupled to rechargeable power source 18. In inductive coupling, charging device 20 is placed near implanted IMD 14 such that a primary coil of charging device 20 is aligned with, i.e., placed over, a secondary coil of IMD 14. Charging device 20 may then generate an electrical current in the primary coil based on a selected power level for charging rechargeable power source 18. As described further below, the power level may be selected to control the temperature of IMD 14 and/or the charge rate of rechargeable power source 18. When the primary and secondary coils are aligned, the electrical current in the primary coil may magnetically induce an electrical current in the secondary coil within IMD 14. Since the secondary coil is associated with and electrically coupled to rechargeable power source 18, the induced electrical current may be used to increase the voltage, or charge level, of rechargeable power source 18. Although inductive coupling is generally described herein, any type of wireless energy transfer may be used to charge rechargeable power source 18.

During the energy transfer process that charges rechargeable power source 18, some of the energy may be converted into heat at rechargeable power source 18 and/or other components of IMD 14. When increased energy levels are used to charge rechargeable power source 18 at a higher rate, the temperature of IMD 14 may also increase. Although the temperature of the IMD 14 housing may not achieve a temperature sufficient to burn or necrose tissue adjacent to the housing of IMD 14, elevated temperatures may be undesirable and uncomfortable over time. Therefore, charging device 20 may control the power levels used to charge rechargeable power source 18 to reduce or minimize any undesirable temperatures of IMD 14 that could be caused by charging rechargeable power source 18. In addition, monitoring the temperature of IMD 14 and/or the temperature of tissue adjacent to the housing of IMD 14 may minimize patient discomfort during the charging process.

In one example, the power level used by charging device 20 to recharge rechargeable power source 18 may be selected or controlled based on a cumulative thermal dose delivered to patient 12 by IMD 14. The cumulative thermal dose may be a metric used to quantify or estimate the total temperature exposure to tissue adjacent to IMD 14. As such, the cumulative thermal dose may be an estimated cumulative thermal dose. In one example, the cumulative thermal dose may be calculated by integrating the tissue temperature over a period of time. The resulting cumulative thermal dose may be used to equate the delivered heat to a certain tissue temperature level for a certain period of time. For example, the clinician may want to limit tissue exposure to heat for 30 minutes at 43 degrees Celsius. However, the temperature of IMD 14 will likely vary from any one temperature over the charging period. Calculation of the cumulative thermal dose may thus allow charging device 20, or IMD 14, to determine when the desired limit to heat exposure is reached even if the actual tissue temperature varies over time. In other examples, the cumulative thermal dose may be calculated by adding the average temperature for multiple segments of the predetermined period of time. In any example, the cumulative thermal dose may be used to determine the total amount of heat or the extent of elevated temperature exposure for tissue surrounding and/or adjacent to IMD 14.

The tissue temperature used to calculate the cumulative thermal dose may be determined using several different techniques. Each technique may result in a cumulative thermal dose that estimates the actual cumulative thermal dose received by patient 12. However, the estimated cumulative thermal dose calculated by system 10 may be substantially similar to the actual cumulative thermal dose received by patient 12. In one example, the tissue temperature may be measured at one or more locations of IMD 14. IMD 14 may include one or more thermocouples, thermistors, or other temperature sensing elements near the inner surface of the housing of IMD 14, built within the housing, or disposed on the external of IMD 14. In other examples, IMD 14 may include one or more temperature sensing elements that extend from the outer surface of IMD 14. This direct tissue temperature measurement may be the most accurate. However, the tissue temperature measurements may need to be transmitted to charging device 20 such that a processor of charging device 20 can calculate the cumulative thermal dose. Alternatively, a processor of IMD 14 may use the measured tissue temperature to calculate the cumulative thermal dose. The processor of IMD 14 may then transmit the cumulative thermal dose such that charging device 20 can select the power level, or the processor of IMD 14 may directly select power level based on the cumulative thermal dose and instruct charging device 20 on the power level to be used for charging.

In another example, the tissue temperature may be indirectly calculated, or estimated, based on a tissue model and the power transmitted to rechargeable power source 18 over a period of time. Charging device 20 may monitor the generated current in the primary coil and the resulting power transmitted from charging device 20 to the secondary coil located in IMD 14. The transmitted power may be calculated using the generated electrical current, estimated based on the generated electrical current and expected energy losses due to heat and misalignment, estimated based on the generated electrical current and energy losses due to misalignment, or some combination therein. In this manner, charging device 20 may unilaterally determine the tissue temperature. Alternatively, IMD 14 may measure the actual electrical current induced in the secondary coil coupled to rechargeable power source 18. Based on this measured current, a processor of IMD 14 may calculate the power transmitted from charging device 20. IMD 14 may then transmit the calculated power transmitted from charging device 20 back to charging device 20.

The measured or estimated power transmitted from charging device 20 to rechargeable power source 18 may then be applied to a tissue model to calculate the expected tissue temperature. The tissue model may be one or more equations that incorporate one or more of the heat capacity of tissue adjacent IMD 14, density of surrounding tissue, inherent body temperature, surface area of the housing of IMD 14, estimated surface area of tissue surrounding IMD 14, depth of IMD 14 from the skin of patient 12, orientation of the secondary coil within patient 12, or any other variable that would affect the temperature of surrounding and/or in immediate contact with the housing of IMD 14. The tissue model may even be modified over time to account for tissue ingrowth, scar tissue, encapsulation, and other tissue changes due to the biological interaction between the housing of IMD 14 and patient 12. The transmitted power may be inputted into the tissue model to calculate an estimation of the tissue temperature as charging device 20 recharges rechargeable power source 18.

Using the transmitted power techniques, the tissue temperature may be calculated by processors of charging device 20, IMD 14, or some combination thereof. For example, charging device 20 may unilaterally calculate the tissue temperature using the tissue model and measured power transmitted to IMD 14. In another example, one or more measured variables may be communicated from IMD 14 to charging device 20 such that charging device can calculate the tissue temperature. IMD 14 may transmit detected alignment of the primary and secondary coils and/or the electrical current induced in the secondary coil. In an alternative embodiment, IMD 14 may measure the transmitted power and calculate the tissue temperature based on that measured power transmitted from charging device 20. IMD 14 may then transmit the calculated tissue temperature to charging device 20, calculate and transmit the cumulative thermal dose to charging device 20 based on the tissue temperature, or even transmit a selected power level for charging device 20 based on the calculated cumulative thermal dose. According to these examples, the processes needed to determine a tissue temperature (e.g., using a measured temperature or tissue model calculation) and calculate the cumulative thermal dose may be performed independently by one of charging device 20 or IMD 14 or collectively through communication between charging device 20 and IMD 14.

As described herein, information may be transmitted between charging device 20 and IMD 14. Therefore, IMD 14 and charging device 20 may communicate via wireless communication using any techniques known in the art. Examples of communication techniques may include, for example, low frequency or radiofrequency (RF) telemetry, but other techniques are also contemplated. In some examples, charging device 20 may include a communication head that may be placed proximate to the patient's body near the IMD 14 implant site in order to improve the quality or security of communication between IMD 14 and charging device 20. Communication between charging device 20 may occur during or separate from power transmission.

The cumulative thermal dose is a metric that may reflect the amount of heat delivered to tissue over a period of time. Since tissue does dissipate heat, the amount of heat delivered to the tissue does not continually compound over the life of patient 12. Instead, the total amount of delivered heat may only be significant over a certain period of time. This period of time may be set by the manufacturer or the clinician to a certain number of minutes, hours, or even days. Generally, the period used to calculate the cumulative thermal dose may be between approximately 10 minutes and 10 days. More specifically, the period used to calculate the cumulative thermal dose may be between approximately one hour and 48 hours. In one example, the period may be set to approximately 24 hours. This period may be a rolling period that extends back from current time. In other words, if the period is 24 hours, the cumulative thermal dose may be the total amount of degree-minutes in the last 24 hours. In other examples, the period of time may be represented as an event. For example, the period of time may be established as a single recharge session (e.g., a continuous transmission of charging power transmitted from charging device 20 to IMD 14). Therefore, the period may be defined by time or events.

The cumulative thermal dose may be utilized by system 10 to control the power transmitted from charging device 20 to IMD 14, the rate of recharging rechargeable power source 18, and the heat generated by IMD 14 during the recharging process. Accordingly, system 10, e.g., one or more processors of charging device 20 and/or IMD 14, may calculate a cumulative thermal dose delivered to patient 12 during charging of rechargeable power source 18 of IMD 14 over a period of time. The one or more processors of system 10 may then select a power level for subsequent charging of the rechargeable power source based on the calculated cumulative thermal dose. Charging device 20 may then charge rechargeable power source 18 with the selected power level. As discussed in greater detail below, the selected power level may change during the charging session to control the heat, and cumulative thermal dose, transmitted to tissue surrounding IMD 14. Although a processor of IMD 14 may select the charging power level, a processor of charging device 20 will be described herein as selecting the charging power level for purposes of illustration.

In one example, charging device 20 may select a high power level when the cumulative thermal dose has not exceeded a thermal dose threshold and select a low power level when the cumulative thermal dose has exceeded the thermal dose threshold. In this manner, the high power level may charge rechargeable power source 18 at a high rate to reduce charging time while increasing the temperature of IMD 14. Once the cumulative thermal dose from the elevated IMD 14 temperature exceeds the thermal dose threshold, charging device 20 may select a low power level to charge rechargeable power source 18 at a slower rate to reduce the temperature of IMD 14. The low power level may be sufficiently minimal so that any increase in temperature of IMD 14 may have minimal or no effect on surrounding tissue.

A high power level and a low power level may be subjective and relative to the charging power that charging device 20 is capable of generating and transmitting to IMD 14. In some cases, the high power level may be the maximum power that charging device 20 can generate. This high power level may be referred to as a "boost" or "accelerated" charging level because of the high rate of charge induced in rechargeable power source 18. This high rate of charge may minimize the amount of time patient 12 needs to recharge rechargeable power source 18. By monitoring the cumulative thermal dose, charging device 20 may charge rechargeable power source 18 with the high power level for a longer period of time without damaging tissue surrounding IMD 14. In other words, merely estimating the amount of time that charging device 20 can charge at the high power level without calculating the actual cumulative thermal dose may expose tissue to an unsafe level of heat or underutilize the high power charging, resulting in longer total charge times. Therefore, using the cumulative thermal dose delivered to patient 12 may allow system 10 to more effectively balance fast charge times and safe heating levels.

In one example, the high power level may be approximately 2.5 Watts and the low power level may be approximately 1.0 milliwatts (mW). An example charge current level may be approximately 100 milliamps (mA) for the high power level and approximately 60 mA for the low power level. The frequency of the charging signal may be independent of the power level, but the pulse width may generally increase with higher power levels assuming a constant H-bridge voltages. An H-bridge circuit may be used as one method to drive the primary coil of charging device 20 with an alternating current. An H-bridge circuit may have alternating pairs of switches (e.g., transistors) which may be gated on and off using pulses. For example, the width of such pulses may be approximately 4000 microseconds (µS) for a high power level and approximately 2000 µS for a low power level with an H-bridge voltage of approximately 10 volts (V). An example primary coil voltage and current for a high power may be approximately 450 V and approximately 800 mA, respectively, and an example primary coil voltage and current for a low power level may be approximately 250 V and approximately 500 mA. These values are merely examples, and other examples, may include higher or lower values in accordance with the techniques described herein.

The thermal dose threshold may be the maximum cumulative thermal dose identified as still being safe to patient 12. In other words, the thermal dose threshold may be established or selected to prevent tissue from being heated to an elevated level and duration that could be uncomfortable or undesirable. The thermal dose threshold may be preset by the manufacturer or selected by a clinician. The thermal dose threshold may also be modified over time as needed. In some examples, the thermal dose threshold may not be set to the maximum safe dose. Instead, the thermal dose threshold may be set to a lower value to establish a safety margin below the thermal dose threshold that minimizes potential overheating of tissue.

The thermal dose threshold may be based on equivalent heating of the tissue at a certain temperature for a predetermined amount of time. In other words, the thermal dose threshold may be expressed as the total degrees over time in elevated temperature. In one example, the thermal dose threshold may be selected as the equivalent to tissue at 43 degrees Celsius for 30 minutes. In another example, the thermal dose threshold may be selected as the equivalent to tissue at 43 degrees Celsius for 50 minutes. In an alternative example, the thermal dose threshold may be selected as the equivalent to tissue at 41.5 degrees Celsius for 4 hours. These thresholds may be summed for comparison to the cumulative thermal dose. For example, tissue at 43 degrees Celsius for 30 minutes may be expressed by a single value after summing or integrating the tissue temperature elevation (e.g., the difference between 43 degrees Celsius and normal body temperature of 37 degrees Celsius) over the time limit. When the cumulative thermal dose is calculated in a similar manner, the cumulative thermal dose may be compared to the thermal dose threshold as charging device 20 recharges rechargeable power source 18.

The cumulative thermal dose may be calculated by the following equation (1).

$$CEM43 = \sum_{i=1}^{N} R^{(43-T_i)} t_i \quad (1)$$

"CEM 43" may refer to the cumulative equivalent minutes at 43 degrees Celsius for constant temperature epochs (e.g., reference data). $T_i$ is the measured temperature in degrees Celsius, and $t_1$ is the duration of time in minutes. R is a characterizing parameter, or constant, that may be set to 0.25 for temperatures less than 43 degrees Celsius. The value of R may be determined experimentally based on known cell and/or tissue characteristics, and R may be a different value in other examples. In one example, a CEM 43 limit of 5 minutes may be used as cumulative thermal dose threshold and the power level may be chosen such that the cumulative thermal dose of the recharge session may remain lower than the set cumulative thermal dose threshold. In one example, the tissue temperature may be limited to 42 degrees Celsius for the entire recharge session by selecting a certain power level of charging, and the thermal dose threshold would be reached in 20 minutes (e.g., (0.25^(43−42)*20=5 minutes)). Incorporating rising and falling temperatures over time that occur when charging may be taken into effect (e.g., integrating temperature over time) to allow for longer recharge durations than would be possible by estimating a constant temperature at any particular power level.

Although charging device 20 may select between two power levels based on the cumulative thermal dose, charging device 20 may select between three or more discrete power levels or select the power level from a continual range of available power levels. For example, charging device 20 may select between a high, medium, low, and zero (e.g., no transmitted power) power levels to minimize charging times and minimize uncomfortable or undesirable temperatures in surrounding tissue. In another example, charging device 20 may continually adjust the power level in small increments, where the increments are established by the available resolution of the current able to be generated in the primary coil of charging device 20. Therefore, these more adjustable power levels may result in a power level curve over time as opposed to individual steps in power levels that would be present using only high and low power levels. In any example, the transmitted power from charging device 20 to IMD 14 may be varied based on the calculated cumulative thermal dose.

In another example, charging device 20 may select a zero power level when the cumulative thermal dose has exceeded the thermal dose threshold. This zero power level would stop charging rechargeable power source 18 because charging device 20 would terminate current to the primary coil in response to the selection of the zero power level. Although low power levels may be used to charge rechargeable power source 18 at low rates (e.g., a trickle charge), terminating charging with the zero power level may allow IMD 14 to cool down at the fastest rate and minimize any additional heating of the tissue surrounding IMD 14. In addition, the zero power level may be selected when rechargeable power source 18 has been fully charged.

In an additional example, charging device 20 may reduce charging power levels in anticipation of meeting or exceeding the thermal dose threshold. Charging device 20 may calculate an available thermal dose by subtracting the cumulative thermal dose from the thermal dose threshold. In other words, the available thermal dose may be the thermal dose remaining before the cumulative thermal dose exceeds the thermal dose threshold. This available thermal dose may be used to reduce power levels of charging prior to exceeding the thermal dose threshold. The available thermal dose may be compared to a high power dose requirement that indicates the power should be reduced because the cumulative thermal dose is approaching the thermal dose threshold. The high power dose requirement may be set to a percentage of the thermal dose threshold, e.g., between 70 percent and 95 percent of the thermal dose threshold. The high power dose requirement may instead be set to a certain absolute value below the thermal dose threshold. Using these guidelines, charging device 20 may select a high power level when the available thermal dose is greater than the high power dose requirement. Charging device 20 may then select a low power level when the available thermal dose is less than the high power dose requirement. Charging device 20 may subsequently continue to charge rechargeable power source 18 with the low power level or even terminate charging once the cumulative thermal dose exceeds the thermal dose threshold.

In other examples, system 10 may employ a lockout period that limits the time charging device 20 can charge rechargeable power source 18 with the high power level. The lockout period may begin after a high power level is used to charge rechargeable power source 18, and the high power level may only be used again once the lockout period expires or elapses. In this manner, charging device 20 may initiate the lockout period after charging rechargeable power source 18 with the high power level such that the lockout period prevents selection of the high power level. The duration of the lockout period may be based on a previous charging time with the high power level. In other words, the lockout period may be set to a longer period of time when the high power level was used for a longer period of time. In other examples, the lockout period may be set to a single time period regardless of how long charging was performed with the high power level.

In some examples, IMD 14 may directly adjusting the power level for charging (e.g., limit the charge current) instead of relying on a change in power level at charging device 20. For example, IMD 14 may employ a circuit that may change from full-wave rectification to half-wave rectification to reduce the charge rate and temperature of IMD 14 during charging. In other words, IMD 14 may utilize half-wave rectification as a means to reduce the electrical current delivered to rechargeable power supply 18 instead of reducing the overall power received by IMD 14. Alternatively, IMD 14 may employ other mechanisms such as current and/or voltage limiters that may limit the charging rate of rechargeable power supply 18.

Although an implantable rechargeable power source 18 is generally described herein, techniques of this disclosure may also be applicable to a rechargeable power source 18 that is not implanted. For example, rechargeable power source 18 may be external to the skin of patient 12 and in physical contact with the skin. Therefore, charging device 20 may control the charging of rechargeable power source 18 with the calculated cumulative thermal dose even when the power source is external to patient 12. However, tissue models and thresholds may be modified to configure charging device 20 for external charging use.

Figure 2:
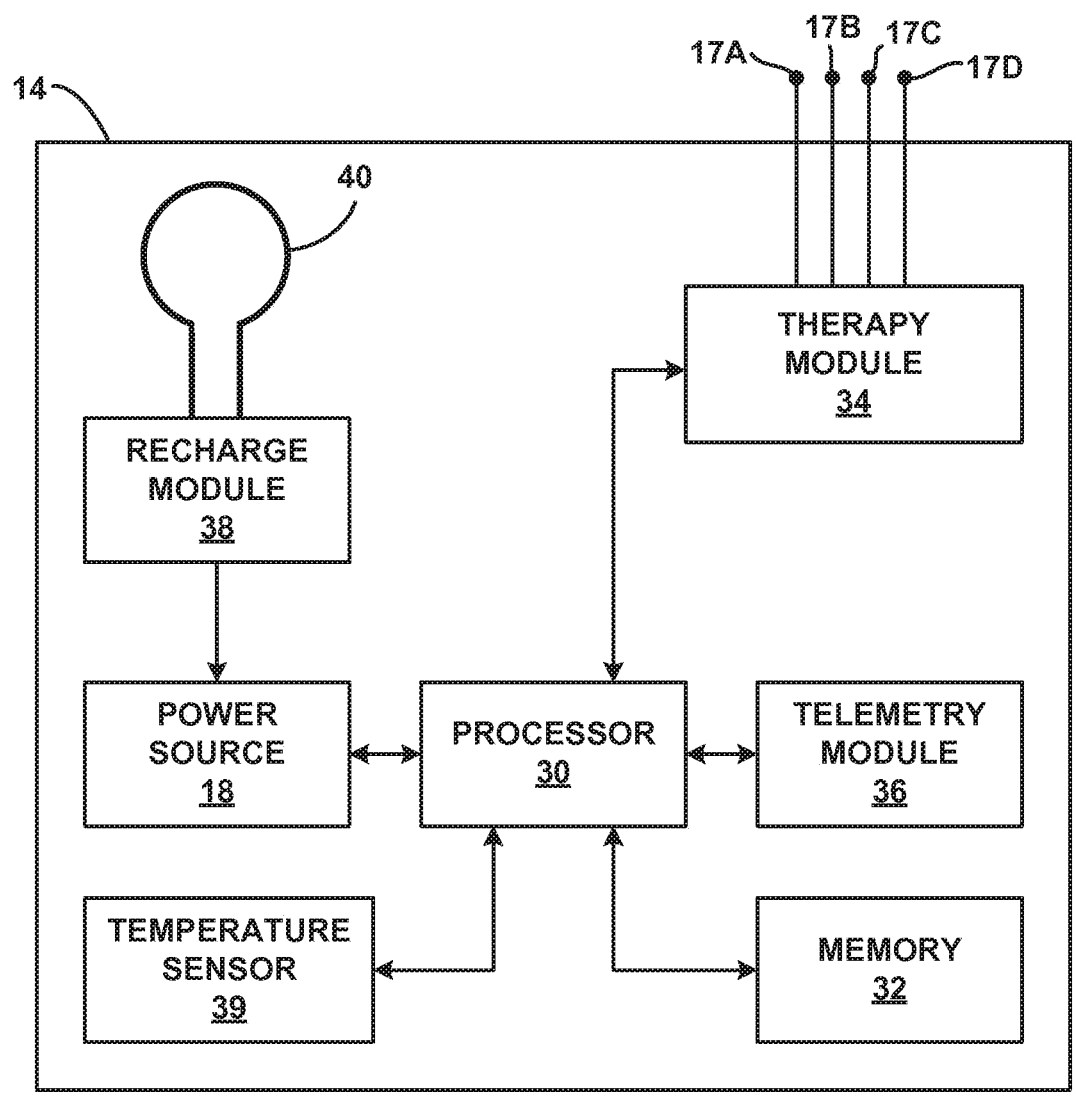
FIG. 2 is a block diagram of the example IMD of FIG. 1.

FIG. 2 is a block diagram illustrating example components of IMD 14. In the example of FIG. 2, IMD 14 includes temperature sensor 39, coil 40, processor 30, therapy module 34, recharge module 38, memory 32, telemetry module 36, and rechargeable power source 18. In other examples, IMD 14 may include a greater or fewer number of components. For example, in some examples, such as examples in which the tissue temperature is calculated from the transmitted power, IMD 14 may not include temperature sensor 39.

In general, IMD 14 may comprise any suitable arrangement of hardware, alone or in combination with software and/or firmware, to perform the various techniques described herein attributed to IMD 14 and processor 30. In various examples, IMD 14 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 also, in various examples, may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 30, therapy module 34, recharge module 38, and telemetry module 36 are described as separate modules, in some examples, processor 30, therapy module 34, recharge module 38, and telemetry module 36 are functionally integrated. In some examples, processor 30, therapy module 34, recharge module 38, and telemetry module 36 correspond to individual hardware units, such as ASICs, DSPs, FPGAs, or other hardware units.

Memory 32 may store therapy programs or other instructions that specify therapy parameter values for the therapy provided by therapy module 34 and IMD 14. In some examples, memory 32 may also store temperature data from temperature sensor 39, instructions for recharging rechargeable power source 18, tissue models, thresholds, instructions for communication between IMD 14 and charging device 20, or any other instructions required to perform tasks attributed to IMD 14. In this manner, memory 32 may be configured to store a tissue model such that processor 30 may be configured to calculate the tissue temperature surrounding IMD 14 based on the tissue model and power received by secondary coil 40 and rechargeable power source 18 over a period of time.

Generally, therapy module 34 may generate and deliver electrical stimulation under the control of processor 30. In some examples, processor 30 controls therapy module 34 by accessing memory 32 to selectively access and load at least one of the stimulation programs to therapy module 34. For example, in operation, processor 30 may access memory 32 to load one of the stimulation programs to therapy module 34. In such examples, relevant stimulation parameters may include a voltage amplitude, a current amplitude, a pulse rate, a pulse width, a duty cycle, or the combination of electrodes 17A, 17B, 17C, and 17D that therapy module 34 uses to deliver the electrical stimulation signal. Although therapy module 34 may be configured to generate and deliver electrical stimulation therapy via one or more of electrodes 17A, 17B, 17C, and 17D of lead 16, therapy module 34 may be configured to provide different therapy to patient 12. For example therapy module 34 may be configured to deliver drug delivery therapy via a catheter. These and other therapies may be provided by IMD 14.

IMD also includes components to receive power from charging device 20 to recharge rechargeable power source 18 when rechargeable power source 18 has been at least partially depleted. As shown in FIG. 2, IMD 14 includes secondary coil 40 and recharge module 38 coupled to rechargeable power source 18. Recharge module 38 may be configured to charge rechargeable power source 18 with the selected power level determined by either processor 30 or charging device 20. Although processor 30 may provide some commands to recharge module 38 in some examples, processor 30 may not need to control any aspect of recharging.

Secondary coil 40 may include a coil of wire or other device capable of inductive coupling with a primary coil disposed external to patient 12. Although primary coil 48 is illustrated as a simple loop of in FIG. 3, primary coil 48 may include multiple turns of wire. Secondary coil may include a winding of wire configured such that an electrical current can be induced within secondary coil 40 from a magnetic field. The induced electrical current may then be used to recharge rechargeable power source 18. In this manner, the electrical current may be induced in secondary coil 40 associated with rechargeable power source 18. The induction may be caused by electrical current generated in the primary coil of charging device 20 and based on the selected power level. The coupling between secondary coil 40 and the primary coil of charging device 20 may be dependent upon the alignment of the two coils. Generally, the coupling efficiency increases when the two coils share a common axis and are in close proximity to each other. Charging device 20 and/or IMD 14 may provide one or more audible tones or visual indications of the alignment.

Although inductive coupling is generally described as the method for recharging rechargeable power source 18, other wireless energy transfer techniques may alternatively be used. Any of these techniques may generate heat in IMD 14 such that the charging process can be controlled using the calculated cumulative thermal dose as feedback.

Recharge module 38 may include one or more circuits that filter and/or transform the electrical signal induced in secondary coil to an electrical signal capable of recharging rechargeable power source 18. For example, in alternating current induction, recharge module 38 may include a half-wave rectifier circuit and/or a full-wave rectifier circuit configured to convert alternating current from the induction to a direct current for rechargeable power source 18. The full-wave rectifier circuit may be more efficient at converting the induced energy for rechargeable power source 18. However, a half-wave rectifier circuit may be used to store energy in rechargeable power source 18 at a slower rate. In some examples, recharge module 38 may include both a full-wave rectifier circuit and a half-wave rectifier circuit such that recharge module 38 may switch between each circuit to control the charging rate of rechargeable power source 18 and temperature of IMD 14.

In some examples, recharge module 38 may include a measurement circuit configured to measure the current and/or voltage induced during inductive coupling. This measurement may be used to measure or calculate the power transmitted to IMD 14 from charging device 20. In some examples, the transmitted power may be used to approximate the temperature of IMD 14 and that of the surrounding tissue. This method may be used to indirectly measure the temperature of tissue in contact with the housing of IMD 14. In other examples, IMD 14 may estimate the transmitted power using the measured voltage or current after recharge module 38 or the charging rate of rechargeable power source 18.

Rechargeable power source 18 may include one or more capacitors, batteries, or other energy storage devices. Rechargeable power source 18 may then deliver operating power to the components of IMD 14. In some examples, rechargeable power source 18 may include a power generation circuit to produce the operating power. Rechargeable power source 18 may be configured to operate through hundreds or thousands of discharge and recharge cycles. Rechargeable power source 18 may also be configured to provide operational power to IMD 14 during the recharge process. In some examples, rechargeable power source 18 may be constructed with materials to reduce the amount of heat generated during charging. In other examples, IMD 14 may be constructed of materials that may help dissipate generated heat at rechargeable power source 18, recharge module 38, and/or secondary coil 40 over a larger surface area of the housing of IMD 14.

Although rechargeable power source 18, recharge module 38, and secondary coil 40 are shown as contained within the housing of IMD 14, at least one of these components may be disposed outside of the housing. For example, secondary coil 40 may be disposed outside of the housing of IMD 14 to facilitate better coupling between secondary coil 40 and the primary coil of charging device 20. These different configurations of IMD 14 components may allow IMD 14 to be implanted in different anatomical spaces or facilitate better inductive coupling alignment between the primary and secondary coils.

IMD 14 may also include temperature sensor 39. Temperature sensor 39 may include one or more temperature sensors (e.g., thermocouples or thermistors) configured to measure the temperature of IMD 14. Temperature sensor 39 may be disposed internal of the housing of IMD 14, contacting the housing, formed as a part of the housing, or disposed external of the housing. As described herein, temperature sensor 39 may be used to directly measure the temperature of IMD 14 and/or tissue surrounding and/or contacting the housing of IMD 14. Processor 30, or charging device 20, may use this temperature measurement as the tissue temperature feedback to determine the cumulative thermal dose provided to tissue during charging of rechargeable power source 18. Although a single temperature sensor may be adequate, multiple temperature sensors may provide a better temperature gradient or average temperature of IMD 14. The various temperatures of IMD 14 may also be modeled and provided to determine the cumulative thermal dose. Although processor 30 may continually measure temperature using temperature sensor 39, processor 30 may conserve energy by only measuring temperature during recharge sessions. Further, temperature may be sampled at a rate necessary to calculate the cumulative thermal dose, but the sampling rate may be reduced to conserve power as appropriate.

Processor 30 may also control the exchange of information with charging device 20 and/or an external programmer using telemetry module 36. Telemetry module 36 may be configured for wireless communication using radio frequency protocols or inductive communication protocols. Telemetry module 36 may include one or more antennas configured to communicate with charging device 20, for example. Processor 30 may transmit operational information and receive therapy programs or therapy parameter adjustments via telemetry module 36. Also, in some examples, IMD 14 may communicate with other implanted devices, such as stimulators, control devices, or sensors, via telemetry module 36. In addition, telemetry module 36 may be configured to transmit the measured tissue temperatures from temperature sensor 39, for example. In some examples, the tissue temperature may be measured adjacent to rechargeable power source 18. In this manner, charging device 20 may calculate the cumulative thermal dose using the transmitted tissue temperature. In other examples, processor 30 may calculate the cumulative thermal dose and transmit the calculated cumulative thermal dose using telemetry module 36.

In other examples, processor 30 may transmit additional information to charging device 20 related to the operation of rechargeable power source 18. For example, processor 30 may use telemetry module 36 to transmit indications that rechargeable power source 18 is completely charged, rechargeable power source 18 is fully discharged, or any other charge status of rechargeable power source 18. Processor 30 may also transmit information to charging device 20 that indicates any problems or errors with rechargeable power source 18 that may prevent rechargeable power source 18 from providing operational power to the components of IMD 14.

Figure 3:
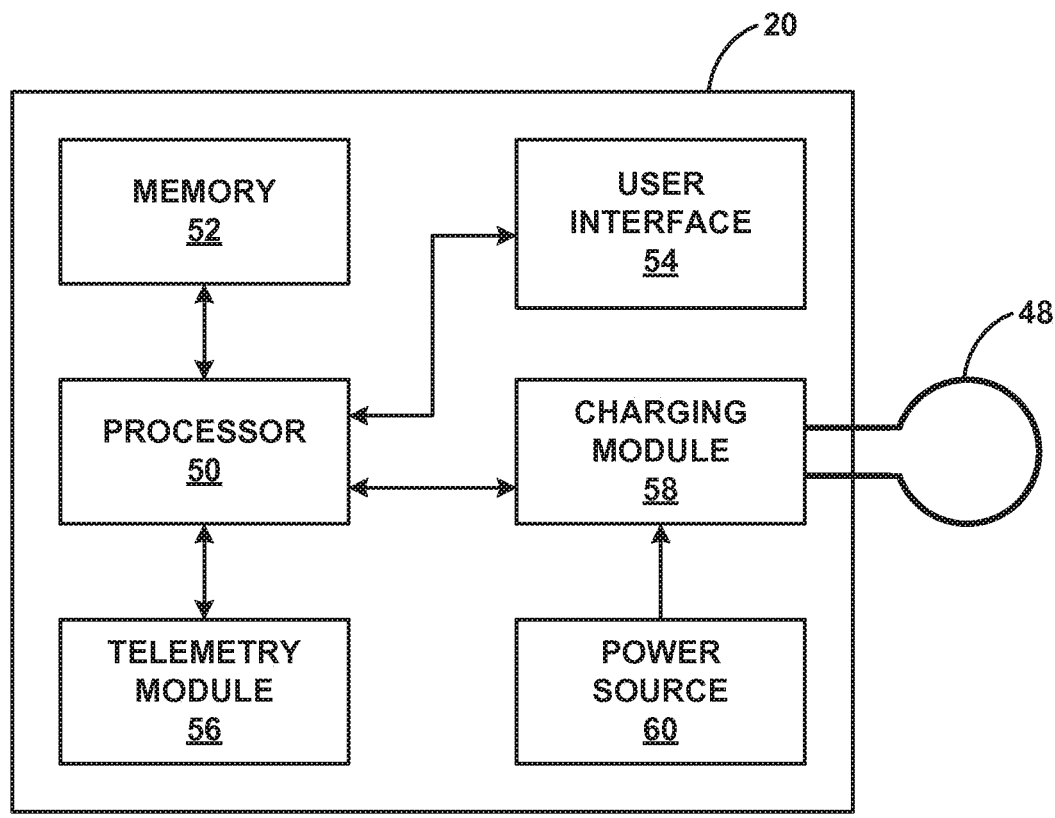
FIG. 3 is a block diagram of the example external charging device of FIG. 1.

FIG. 3 is a block diagram of the example external charging device 20. While charging device 20 may generally be described as a hand-held device, charging device 20 may be a larger portable device or a more stationary device. In addition, in other examples, charging device 20 may be included as part of an external programmer or include functionality of an external programmer. In addition, charging device 20 may be configured to communicate with an external programmer. As illustrated in FIG. 3, charging device 20 may include a processor 50, memory 52, user interface 54, telemetry module 56, power module 58, coil 48, and power source 60. Memory 52 may store instructions that, when executed by processor 50, cause processor 50 and external charging device 20 to provide the functionality ascribed to external charging device 20 throughout this disclosure.

In general, charging device 20 comprises any suitable arrangement of hardware, alone or in combination with software and/or firmware, to perform the techniques attributed to charging device 20, and processor 50, user interface 54, telemetry module 56, and charging module 58 of charging device 20. In various examples, charging device 20 may include one or more processors, such as one or more microprocessors, DSPs, ASICs, FPGAs, or any other equivalent integrated or discrete logic circuitry, as well as any combinations of such components. Charging device 20 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processor 50 and telemetry module 56 are described as separate modules, in some examples, processor 50 and telemetry module 56 are functionally integrated. In some examples, processor 50 and telemetry module 56 and charging module 58 correspond to individual hardware units, such as ASICs, DSPs, FPGAs, or other hardware units.

Memory 52 may store instructions that, when executed by processor 50, cause processor 50 and charging device 20 to provide the functionality ascribed to charging device 20 throughout this disclosure. For example memory 52 may include instructions that cause processor 50 to calculate cumulative thermal doses, establish thresholds, select power levels based on the cumulative thermal doses and otherwise control charging module 58, communicate with IMD 14, or instructions for any other functionality. In addition, memory 52 may include a record of selected power levels, calculated cumulative thermal doses, or any other data related to charging rechargeable power source 18. Processor 50 may, when requested, transmit any of this stored data in memory 52 to another computing device for review or further processing.

In some examples, memory 52 may be configured to store data representative of a tissue model used by processor 50 to calculate the tissue temperature based on the tissue model and power transmitted to rechargeable power source 18 over a period of time. The tissue model may indicate how temperate of tissue surrounding IMD 14 changes over time based on, i.e., as a function of, power received from primary coil 48. Therefore, processor 50 may be able to estimate the tissue temperature without direct measurement of the temperature of tissue surrounding the housing of IMD 14.

User interface 54 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processor 50 may present and receive information relating to the charging of rechargeable power source 18 via user interface 54. For example, user interface 54 may indicate when charging is occurring, quality of the alignment between coils 40 and 48, the selected power level, current charge level of rechargeable power source 18, duration of the current recharge session, anticipated remaining time of the charging session, or any other information. Processor 50 may receive some of the information displayed on user interface 54 from IMD 14 in some examples.

User interface 54 may also receive user input via user interface 54. The input may be, for example, in the form of pressing a button on a keypad or selecting an icon from a touch screen. The input may request starting or stopping a recharge session, a desired level of charging, or one or more statistics related to charging rechargeable power source 18 (e.g., the cumulative thermal dose). In this manner, user interface 54 may allow the user to view information related to the charging of rechargeable power source 18 and/or receive charging commands.

Charging device 20 also includes components to transmit power to recharge rechargeable power source 18 associated with IMD 14. As shown in FIG. 3, charging device 20 includes primary coil 48 and charging module 58 coupled to power source 60. Charging module 58 may be configured to generate an electrical current in primary coil 48 from voltage stored in power source 60. Although primary coil 48 is illustrated as a simple loop in FIG. 3, primary coil 48 may include multiple turns of wire. Charging module 58 may generate the electrical current according to a power level selected by processor 50 based on the cumulative thermal dose. As described herein, processor 50 may select a high power level, low power level, or a variety of different power levels to control the rate of recharge in rechargeable power source 18 and the temperature of IMD 14. In some examples, processor 50 may control charging module 58 based on a power level selected by processor 30 of IMD 14.

Primary coil 48 may include a coil of wire, e.g., having multiple turns, or other device capable of inductive coupling with a secondary coil 40 disposed within patient 12. Primary coil 48 may include a winding of wire configured such that an electrical current generated within primary coil 48 can produce a magnetic field configured to induce an electrical current within secondary coil 40. The induced electrical current may then be used to recharge rechargeable power source 18. In this manner, the electrical current may be induced in secondary coil 40 associated with rechargeable power source 18. The coupling efficiency between secondary coil 40 and primary coil 48 of charging device 20 may be dependent upon the alignment of the two coils. Generally, the coupling efficiency increases when the two coils share a common axis and are in close proximity to each other. User interface 54 of charging device 20 may provide one or more audible tones or visual indications of the alignment.

Charging module 58 may include one or more circuits that generate an electrical signal, and an electrical current, within primary coil 48. Charging module 58 may generate an alternating current of specified amplitude and frequency in some examples. In other examples, charging module 58 may generate a direct current. In any case, charging module 58 may be capable of generating electrical signals, and subsequent magnetic fields, to transmit various levels of power to IMD 14. In this manner charging module 58 may be configured to charge rechargeable power source 18 of IMD 14 with the selected power level.

The power level that charging module 58 selects for charging may be used to vary one or more parameters of the electrical signal generated for coil 48. For example, the selected power level may specify a wattage, electrical current of primary coil 48 or secondary coil 40, current amplitude, voltage amplitude, pulse rate, pulse width, or any other parameter that may be used to modulate the power transmitted from coil 48. In this manner, each power level may include a specific parameter set that specifies the signal for each power level. Changing from one power level to another power level, e.g., a high power level to a low power level, may include adjusting one or more parameters. The parameters of each power level may be selected based on hardware characteristics of charging device 20 and/or IMD 14.

Power source 60 may deliver operating power to the components of charging device 20. Power source 60 may also deliver the operating power to drive primary coil 48 during the charging process. Power source 60 may include a battery and a power generation circuit to produce the operating power. In some examples, the battery may be rechargeable to allow extended portable operation. In other examples, power source 60 may draw power from a wired voltage source such as a consumer or commercial power outlet.

Although power source 60, charging module 58 are shown within a housing of charging device 20 and primary coil 48 is shown external to charging device 20, different configurations may also be used. For example, primary coil 48 may also be disposed within the housing of charging device 20. In another example, power source 60, charging module 58, and primary coil 48 may be all located external to the housing of charging device 20 and coupled to charging device 20.

Telemetry module 56 supports wireless communication between IMD 14 and charging device 20 under the control of processor 50. Telemetry module 56 may also be configured to communicate with another computing device via wireless communication techniques, or direct communication through a wired connection. In some examples, telemetry module 56 may be substantially similar to telemetry module 36 of IMD 14 described herein, providing wireless communication via an RF or proximal inductive medium. In some examples, telemetry module 56 may include an antenna, which may take on a variety of forms, such as an internal or external antenna.

Examples of local wireless communication techniques that may be employed to facilitate communication between charging device 20 and IMD 14 include RF communication according to the 802.11 or Bluetooth specification sets or other standard or proprietary telemetry protocols. In this manner, other external devices may be capable of communicating with charging device 20 without needing to establish a secure wireless connection. As described herein, telemetry module 56 may be configured to receive a measured tissue temperature from IMD 14. The tissue temperature may be measured adjacent to rechargeable power source 18, such as near the housing of IMD 14 or external of the housing. Although IMD 14 may measure the tissue temperature, one or more different implantable temperature sensors (e.g., standalone implantable temperature sensing devices) may independently measure the tissue temperature at different positions and transmit the temperature to charging device 20. In some examples, multiple temperature readings by IMD 14 may be averaged or otherwise used to produce a single temperature value that is transmitted to charging device 20. The temperature may be sampled and/or transmitted at different rates, e.g., on the order of microseconds, milliseconds, seconds, minutes, or even hours. Processor 50 may then use the received tissue temperature to calculate the cumulative thermal dose.

Figure 4:
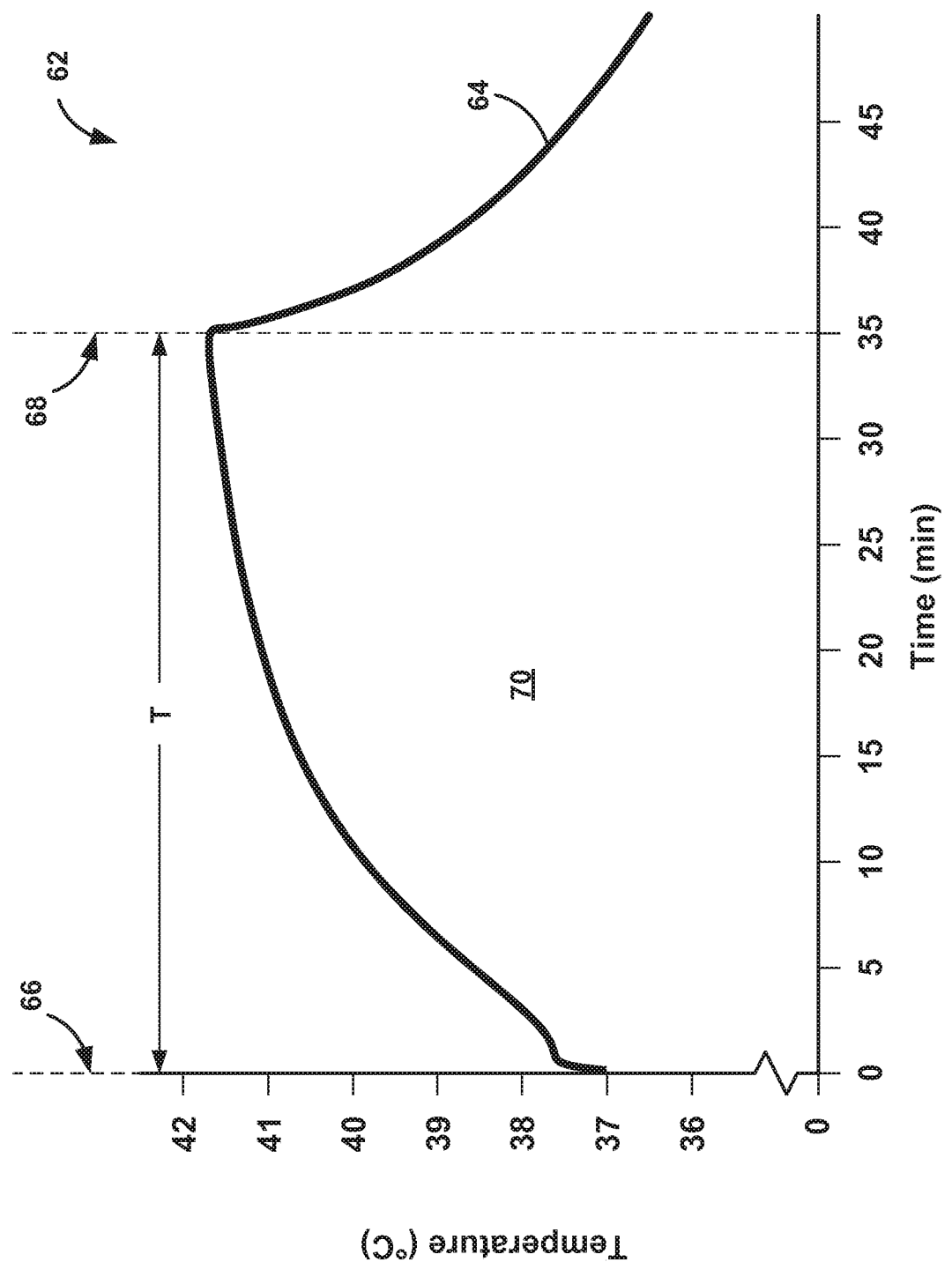
FIG. 4 is a graph of example temperatures generated in a patient during IMD recharging over a period of time.

FIG. 4 is a graph 62 of example temperatures generated in a patient during IMD recharging over a period of time. As shown in FIG. 4, graph 62 includes temperature 64 over time during recharging of rechargeable power source 18. This temperature may be measured within IMD 14, on the housing of IMD 14, or within tissue surrounding IMD 14. Alternatively, the temperature may be calculated based on power transmitted to IMD 14 and a tissue model of how tissue would respond based on the power transmitted over time. Therefore, temperature 64 may be representative of how temperatures in tissue surrounding and/or contacting the housing of IMD 14 may change when rechargeable power source 18 is being recharged with given levels of recharge power.

Graph 62 may indicate how temperature 64 changes when charging device 20 initially selects a high power level for charging and changes to a low power level once the cumulative thermal dose has been reached. Once charging of rechargeable power source 18 begins at the zero minute mark (power level change 66), temperature 64 begins to increase from approximately 37 degrees Celsius. Because charging device 20 transmits power at a high power level, rechargeable power source 18 may charge at a fast rate and the temperature of IMD 14 and surrounding tissue may increase at a relatively high rates as compared to slower charging rates with lower transmitted power levels. Temperature 64 may level out at a certain magnitude based on the transmitted power and the ability of the tissue to dissipate heat.

Time T may indicate the amount of time that it takes for the cumulative thermal dose to reach the thermal dose threshold. The cumulative thermal dose may be determined to be representative of the total amount of heat tissue has been exposed to over a period of time. The cumulative thermal dose may be calculated using a variety of different techniques that indicate this total amount of heat. For example, temperature 64 may be integrated over time to calculate the cumulative thermal dose in degree-minutes. Cumulative thermal dose 70, e.g., the area under the curve of temperature 62, would thus be representative of the total amount of heat delivered to tissue from IMD 14 over time. Since the normal physiological temperature of tissue is approximately 37 degrees Celsius, temperature 64 may only be integrated for temperatures about this 37 degree Celsius floor. However, the cumulative thermal dose may be calculated using any temperature as a floor as long as the thermal dose threshold, or any other thresholds, are established using this floor temperature as well.

In other examples, the cumulative thermal dose may be calculated using alternative techniques. For example, charging device 20 may average temperature 64 for each segment of time (e.g., each minute) and sum the average temperatures for each minute to calculate the cumulative thermal dose. Alternatively, the cumulative thermal dose may be calculated using more complex equations, such as those disclosed herein, that may account for the effect to tissue at different magnitude of temperatures, e.g., weight time differently at different temperatures. As temperature 64 increases, the effects of each incremental change in temperature may cause a disproportional increase in undesirable tissue effects and decrease patient comfort. In other words, each degree change may exponentially decrease the amount of time tissue can safely be exposed to that temperature. For example, it may be safe to expose tissue to 41 degrees Celsius for 4 hours, but a small increase in temperature to 43 degrees may decrease the safe exposure time to only 30 minutes. In this manner, the cumulative thermal dose may be calculated to account for the non-linear relationship between temperature and undesirable side effects over time.

Once the cumulative thermal dose exceeds the thermal dose threshold, charging device 20 may decrease the charging power to a low power level at power level change 68. In the example of FIG. 4, the cumulative thermal dose exceeded the thermal dose threshold at approximately 35 minutes after beginning to charge rechargeable power source 18 with the high power level. The low power level may thus decrease the rate that rechargeable power source 18 is charged and temperature 64 may decrease with this decreased transmitted power. In other examples, charging device 20 may select the low power level before the thermal dose threshold is reached and terminate charging once the thermal dose threshold is reached. In any case, charging device 20 may select the low power level for charging rechargeable power source 18 based on the cumulative thermal dose calculated using temperature 64.

Temperature 64 of graph 62 is only an example of tissue temperature changes due to charging rechargeable power source 18 in IMD 14. In the example of FIG. 4, temperature 64 may increase to approximately 41.5 degrees Celsius prior to reducing the power level for charging. In other examples, temperature 64 may change at faster or slower rates. In addition, temperature 64 may plateau at lower temperatures, plateau at higher temperatures, or not plateau at all during the recharge session. In some examples, temperature 64 may reach temperatures in excess of 42 degrees Celsius or even 43 degrees Celsius. In this manner, the thermal dose threshold, method of calculating the cumulative thermal dose, and other variables for managing the cumulative thermal dose received by patient 12 may be adjusted based on the specific characteristics of charging device 20, IMD 14, and even patient 14.

Figure 5A:
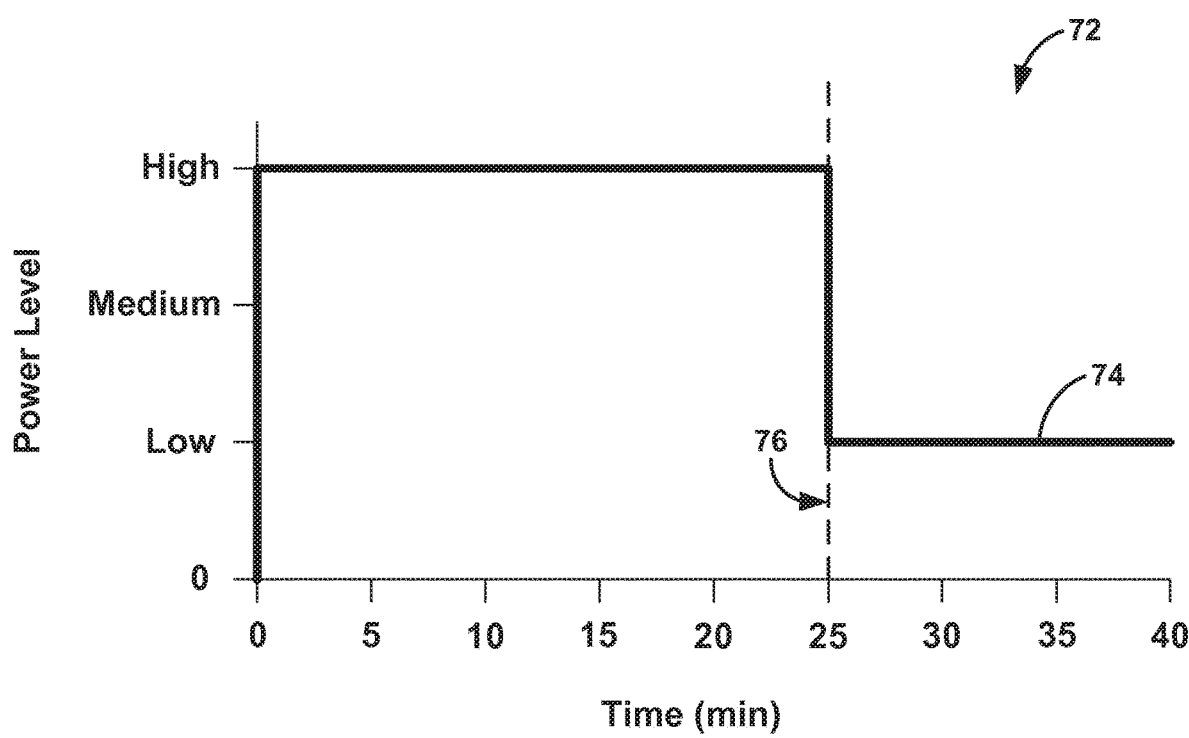
FIGS. 5A and 5B are graphs of example selected power levels for charging and an associated rechargeable power supply charge level due to the selected power levels.
Figure 5B:
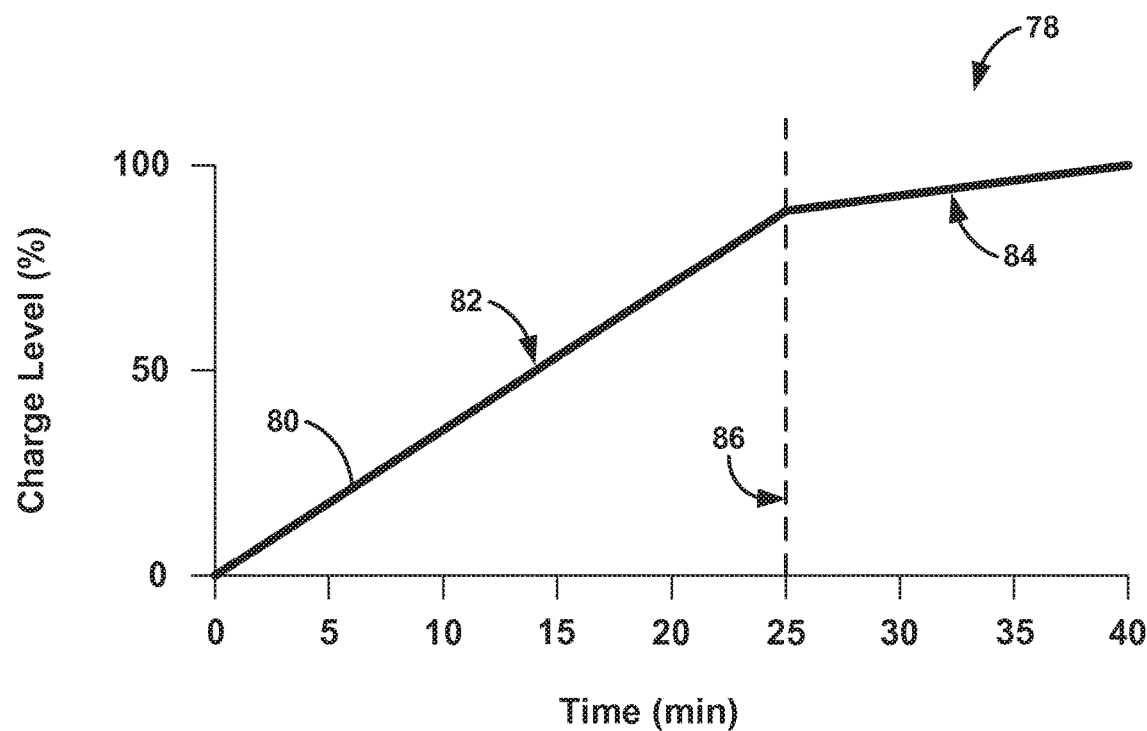

FIGS. 5A and 5B are graphs of example selected power levels for charging and an associated charge level for rechargeable power supply charge 18 due to the selected power levels. Graphs 72 and 78 of FIGS. 5A and 5B may correspond to the changes in temperature illustrated in FIG. 4. In other words, temperature 64 of FIG. 4 is representative of tissue temperature changes due to power levels selected in FIG. 5A and the charging rates of FIG. 5B.

As shown in FIG. 5A, graph 72 illustrates example selected power level 74 of charging device 20 for charging rechargeable power source 18. When charging is initiated, or started, at the zero minute mark, charging device 20 may select a high power level. The initial high power level 74 may be selected to charge rechargeable power source 18 at a fast rate, e.g., a "boost". This fast rate may minimize the amount of time patient 12 may need to recharge rechargeable power source 18. Charging device 20 may use the high power level to transmit energy to IMD 14 until the cumulative thermal dose exceeds the thermal dose threshold.

Charge level change 76 indicates a change from the selected high power level to the low power level. Charging device 20 may select the low power level at charge level change 76 because the cumulative thermal dose exceeded the thermal dose threshold. Then, charging device 20 may continue to charge rechargeable power source 18 with the low power level until rechargeable power source 18 is fully charged. Once rechargeable power source 18 is fully charged, charging device 20 may terminate charging by selecting a zero power level.

Graph 72 indicates high, medium, and low power levels. Although graph 72 indicates that only the high and low power levels are selected, charging device 20 may select the medium power level, or any other power level, in other examples in which various power levels are selected based on the calculated cumulative thermal dose. In other examples, charging device 20 may only select between high and low power levels when charging rechargeable power source 18.

As shown in FIG. 5B, graph 78 illustrates charging rate 80 over time due to varying power levels selected by charging device 20. High rate 82 may be representative of the charging rate of rechargeable power source 18 when charging device 20 selects the high power level for charging. Once the cumulative thermal dose exceeds the thermal dose threshold, charge rate change 86 indicates that the charge rate has been lowered. After charge rate change 86, the low power level induces charging rechargeable power source 18 with low rate 84. Once the charge level for rechargeable power source 18 reaches approximately 100 percent, the charge rate may be reduced to zero because the recharge session may be terminated. In other examples, the low power level may be selected prior to exceeding the thermal dose threshold to better control the exact cumulative thermal dose delivered to patient 12 when the cumulative thermal dose approaches the thermal dose threshold.

Figure 6A:
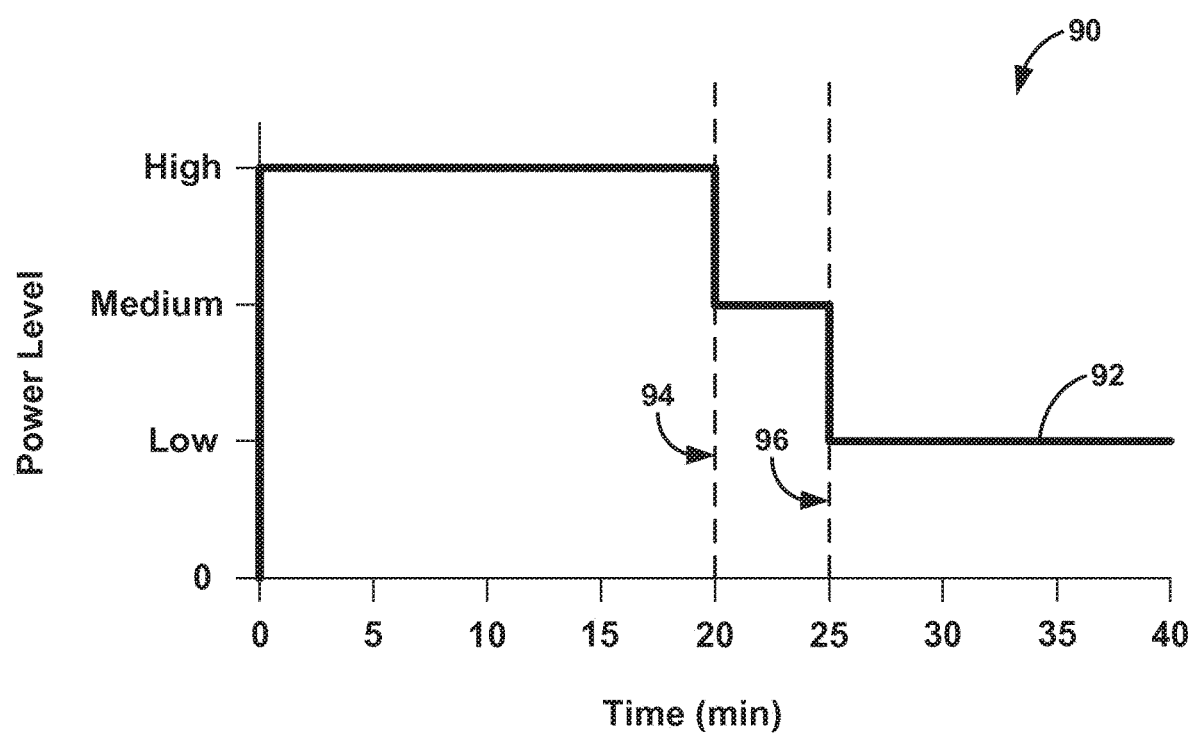
FIGS. 6A and 6B are graphs of example selected power levels for charging and an associated rechargeable power supply charge level due to the selected power levels.
Figure 6B:
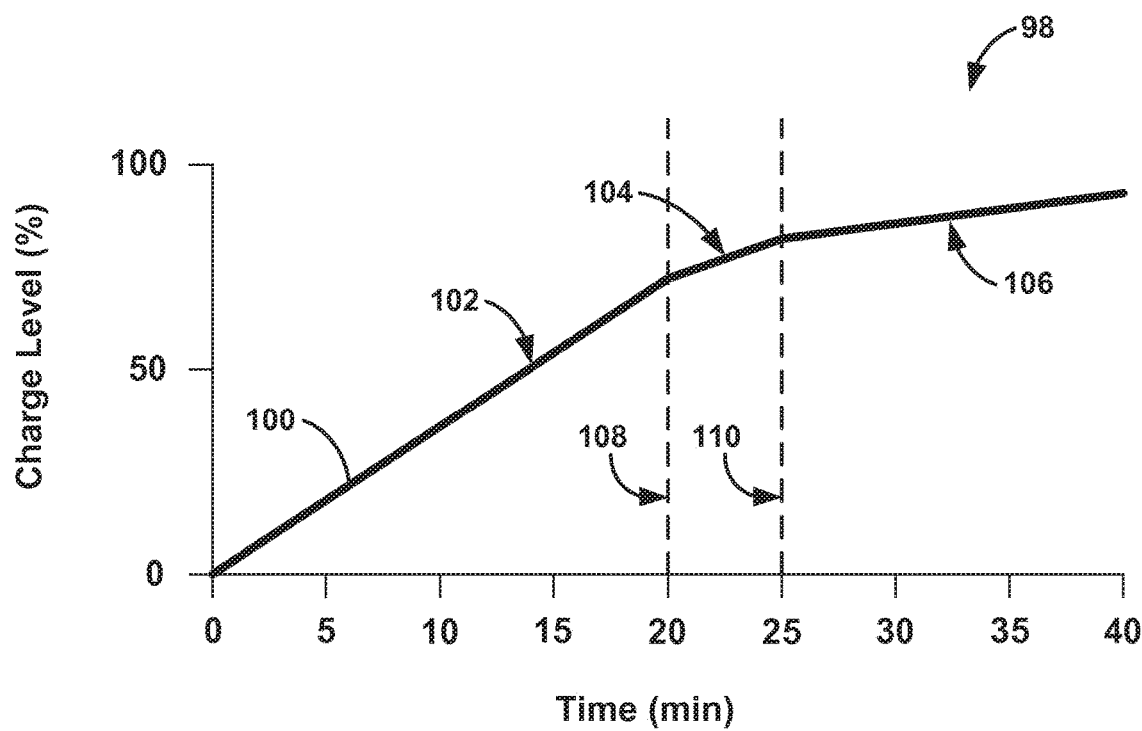

FIGS. 6A and 6B are graphs of example selected power levels for charging and the charge level of associated rechargeable power source 18 due to selected power levels. Graphs 90 and 98 of FIGS. 6A and 6B illustrate power level changes alternative to those of FIGS. 5A and 5B. FIG. 6A illustrates three different power levels for charging and FIG. 6B illustrates the charge rate due to each selected power level. The technique of FIGS. 6A and 6B illustrates changing power levels prior to the cumulative thermal dose reaching the thermal dose threshold.

As shown in FIG. 6A, graph 90 illustrates example selected power level 92 of charging device 20 for charging rechargeable power source 18. When charging is initiated, or started, at the zero minute mark, charging device 20 may select a high power level. The initial high power level between the zero and 20 minute marks may be selected to charge rechargeable power source 18 at a fast rate, e.g., a "boost". This fast rate may minimize the amount of time patient 12 may need to recharge rechargeable power source 18. Charging device 20 may use the high power level to transmit energy to IMD 14 until the calculated cumulative thermal dose begins to approach the thermal dose threshold.

Charging device 20 may calculate an available thermal dose to determine when to select a lower power level for the recharge session. The available thermal dose may be calculated by subtracting the cumulative thermal dose from the thermal dose threshold. Thus, the available thermal dose may indicate the total heat that IMD 14 can still safely provide to surrounding tissue. Charging device 20 may compare the available thermal dose to a high power dose requirement to determine when to reduce the power from the selected high power level. In this manner, charging device 20 may select the high power level when the available thermal dose is greater than the high power dose requirement, e.g., between the zero and 20 minute mark.

Once charging device 20 calculates that the available thermal dose is less than the high power dose requirement, charging device 20 may select the medium power level. Charge level change 94 indicates that the power level was changed from high to medium once the cumulative thermal dose exceeded the high power dose threshold. Then, charging device 20 may charge rechargeable power source 18 with the medium power level between minutes 20 and 25. When the cumulative thermal dose exceeds the thermal dose threshold, charge level change 96 indicates that charging device selects the low power level for additional charging of rechargeable power source 18. Selected power level 92 thus changes as the cumulative thermal dose indicates the amount of heat received by tissue surrounding IMD 14. Charging device 20 may continue to charge rechargeable power source 18 with the low power level until rechargeable power source 18 is fully charged. Once rechargeable power source 18 is fully charged, charging device 20 may terminate charging by selecting a zero power level.

Reducing the charging power level prior to exceeding the thermal dose threshold may allow charging device 20 to ensure that the cumulative thermal dose is not exceeded. In other words, IMD 14 may still radiate heat after the charging power has been decreased. By reducing the power level prior to reaching the thermal dose threshold, IMD 14 may radiate the heat that remains in IMD 14 from the previously higher power level. Once the thermal dose threshold is exceeded, the IMD 14 may have less residual heat to dissipate. Therefore, reducing the power level using the available thermal dose, as opposed to waiting until the thermal dose threshold is exceeded, may allow charging device 20 to better control the total amount of heat to which tissue is exposed.

As shown in FIG. 6B, graph 98 illustrates charging rate 100 over time due to varying power levels selected by charging device 20. High rate 102 may be representative of the charging rate of rechargeable power source 18 when charging device 20 selects the high power level for charging (e.g., the boost rate). Once the cumulative thermal dose exceeds the high power dose requirement, charge rate change 108 indicates that the charge rate has been lowered. After charge rate change 108, the medium power level induces charging rechargeable power source 18 with medium rate 104. Further, once the cumulative thermal dose exceeds the thermal dose threshold, charge rate change 110 indicates that the charge rate has been lowered. After charge rate change 110, the low power level induces charging rechargeable power source 18 with low rate 106. Once the charge level for rechargeable power source 18 reaches approximately 100 percent, the charge rate may be reduced to zero because the recharge session may be terminated.

Graph 90 of FIG. 6A indicates high, medium, and low power levels. Graph 90 indicates that charging device selects between three different power levels based on the cumulative thermal dose calculated from the tissue temperature. In other examples, charging device may utilize a greater number of power levels to change the power level in smaller increments. Therefore, charging device 20 may provide finer control of the recharge rate and the temperature of IMD 14 during the charging session. The finer control of power may allow charging device 20 to gradually change the temperature of IMD 14, e.g., reduce the temperature of IMD 14 such that the cumulative thermal dose does not exceed the thermal dose threshold even after charging stops.

In FIGS. 5A, 5B, 6A, and 6B, charging device 20 selects the low charge level even after the cumulative thermal dose exceeds the thermal dose threshold. In these cases, the low charge level may only cause negligible heating of IMD 14. In other words, the heat produced in IMD 14 during the corresponding low charge rate may cause an insignificant increase to the cumulative thermal dose because the temperature is similar to that of normal body temperature. However, in other example, the low charge level may still generate heat in IMD 14 and contribute to the cumulative thermal dose. In this case, charging device 20 may terminate the charging of rechargeable power source 18 (e.g., select a zero power level).

Figure 7A:
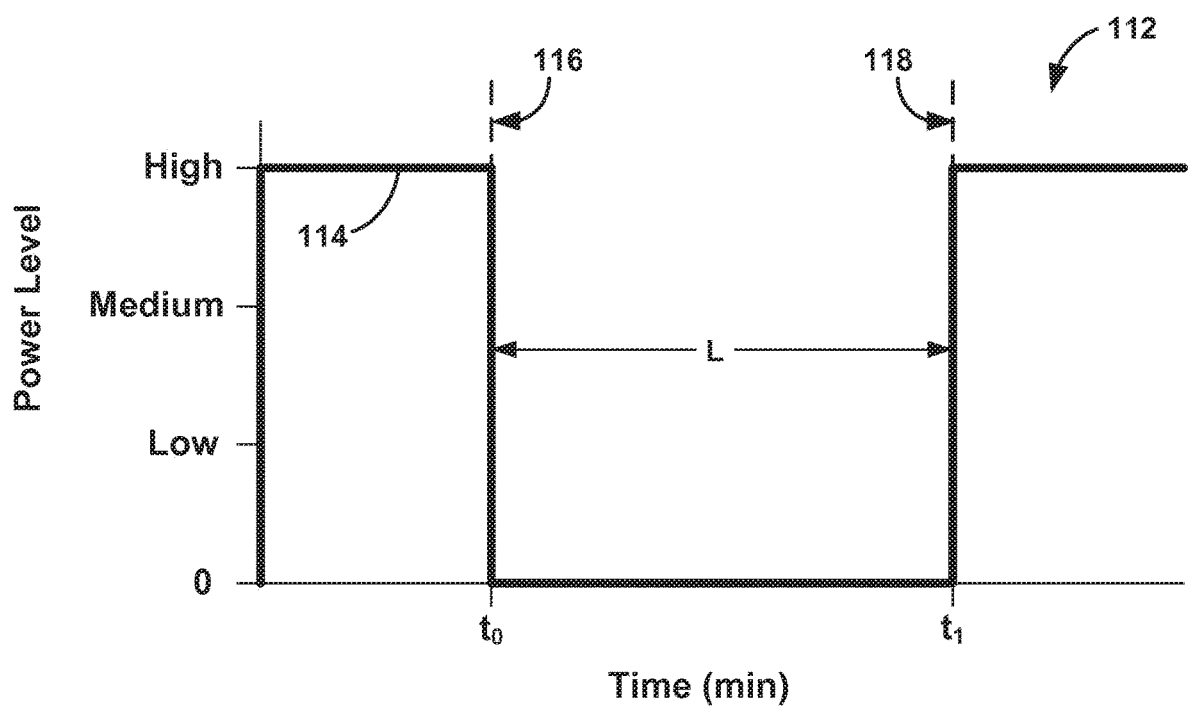
FIGS. 7A and 7B are graphs of example selected power levels due to an imposed lockout period after charging with a high power level.
Figure 7B:
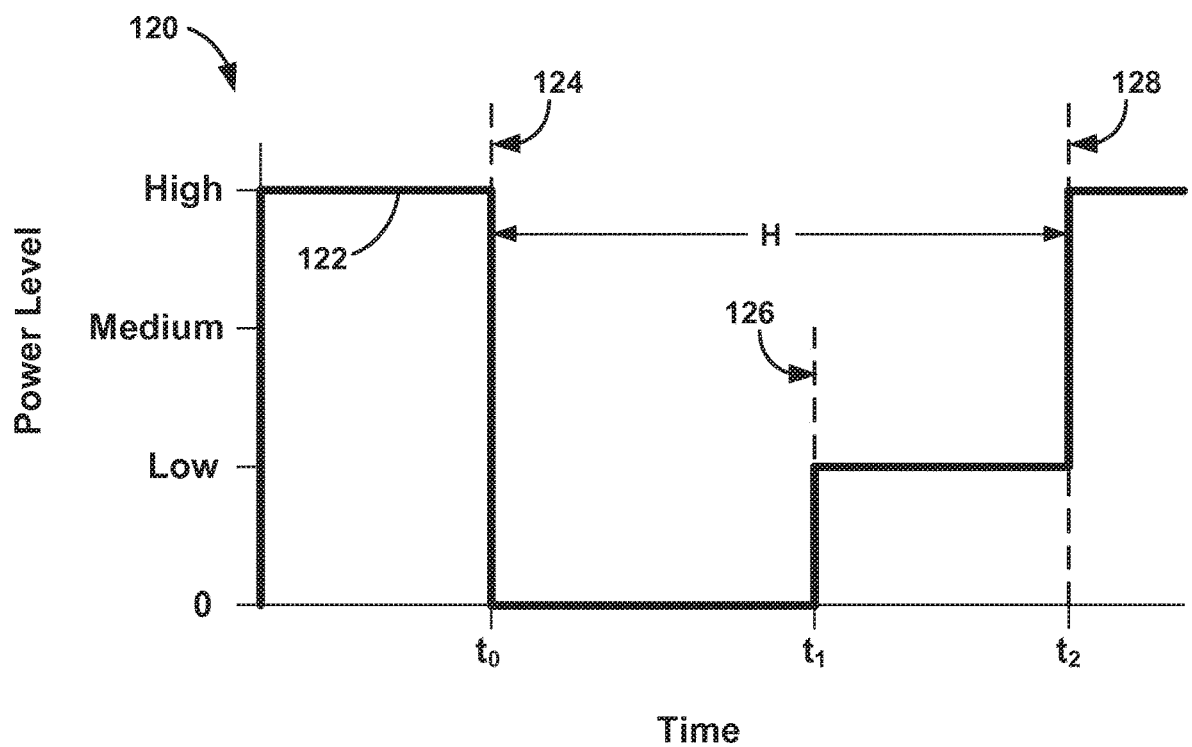

FIGS. 7A and 7B are graphs of example selected power levels due to an imposed lockout period L after charging with a high power level. As shown in FIG. 7A, charging device 20 may charge rechargeable power source 18 with a selected high power level. Charge level 114 of graph 112 indicates, however, that the charge level may change as needed to charge rechargeable power source 18 and limit the cumulative thermal dose delivered to patient 12. Charge level change 116 at to may indicate that charging was stopped because either the cumulative thermal dose exceeded a threshold or rechargeable power source 18 reached a 100 percent charge level.

As shown in the example of FIG. 7A, lockout period L may be implemented after high power levels to limit the use of the high power level and associated relatively high temperatures generated in IMD 14 due to these high charge rates. After the power level is reduced to zero at charge level change 116, lockout period L may prevent any charging of rechargeable power source 18 between $t_0$ and $t_1$. Once lockout period L expires, charging device 20 may again select a power level to charge rechargeable power source 18, such as the high power level indicated after charge level change 118. Although charging device 20 may begin charging rechargeable power source 18 immediately after lockout period L expires, charging is not required to begin immediately. Lockout period L merely enables charging after expiration.

Graph 120 provides charge level 122 varying in response to lockout period H. In the example of FIG. 7B, lockout period H may also be implemented after high power levels to limit the use of the high power level and associated relatively high temperatures generated in IMD 14 due to these high charge rates. After the power level is reduced to zero at charge level change 124, lockout period H may prevent only the selection of high power for charging. Therefore, lockout period H may prevent charging of rechargeable power source 18 with the high power level between $t_0$ and $t_2$. However, lockout period H may not prevent charging device 20 from charging rechargeable power source 18 with a low power level during the lockout period. During lockout period H, charging device 20 may select the low power level at charge level change 126. This low power level selection may allow rechargeable power source 18 to be charged slowly because IMD 14 may not radiate any significant amount of heat during this slow charge.

Once lockout period H expires, charging device 20 may again select a power level to charge rechargeable power source 18, such as the high power level indicated after charge level change 128. Although charging device 20 may begin charging rechargeable power source 18 with the high power level immediately after lockout period H expires, the high power level is merely allowed to be selected any time after the expiration of lockout period H. In some examples, the medium power level, or other power levels, may also be selected during lockout period H. These lower power levels may not significantly increase the temperature of IMD 14 and surrounding tissue while allowing rechargeable power source 18 to still be replenished. Since the high power level may be considered a "boost" in charging in some examples, the high power level may not be needed to recharge rechargeable power source 18.

The duration of the lockout period may vary in different examples and for different purposes. For example, the lockout period may be set to a predetermined period of time that simply limits the frequency of the high power use. This predetermined period may be between approximately 10 minutes and 48 hours. In another example, the lockout period may change based upon the difference between the available thermal dose and the high power dose requirement. Charging device 20 may calculate the difference between the cumulative thermal dose and the thermal dose threshold to determine the available thermal dose. If the high power dose requirement (e.g., the thermal dose required to charge rechargeable power source 18 with the high power level) is greater than the available thermal dose, then the lockout period continues. In this manner, the lockout period may not be a timer that simply allows charging once it expires. In other words, the lockout period may be based on the amount of time charging occurred with the high power level as a proxy for the actual cumulative thermal dose received by patient 12 during the high power level. Alternatively, the lockout period may be based directly on calculated cumulative thermal dose.

In other examples, the lockout period may be initiated only after the cumulative thermal dose has exceeded the thermal dose threshold. Since IMD 14 may continue to expose tissue to heat even after charging stops when the cumulative thermal dose has exceeded the thermal dose threshold, the lockout period may be started to allow the surrounding tissue to recover from the charging session. The lockout period may prevent any charging from occurring or, in some examples, allow charging device 20 to select a low power level for charging with minimal heat generation. Alternatively, charging device 20 may implement multiple lockout period. For example, a full lockout period may prevent any charging from occurring while a high power lockout period may only prevent charging device 20 from selecting the high power level. These multiple timers may operate simultaneously.

Figure 8:
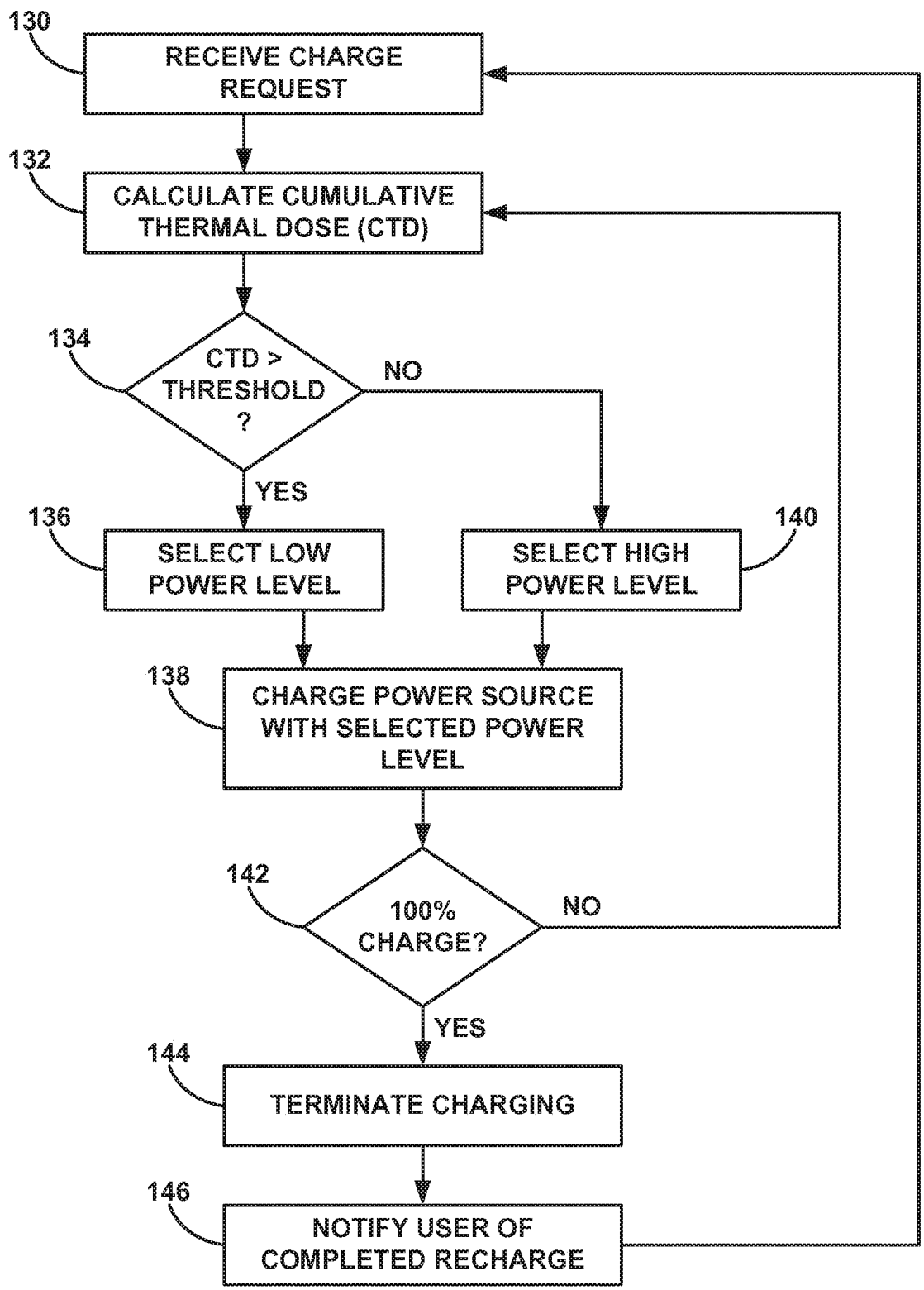
FIG. 8 is a flow diagram that illustrates an example technique for selecting a power level for charging an implantable rechargeable power source based on a calculated cumulative thermal dose.

FIG. 8 is a flow diagram that illustrates an example technique for selecting a power level for charging implantable rechargeable power source 18 based on a calculated cumulative thermal dose. Although processor 50 of charging device 20 will be described as generally performing the technique of FIG. 8, the technique of FIG. 8 may instead be performed by a combination of processors 30 and 50, in other examples.

A charging session for rechargeable power source 18 may begin when processor 50 receives a charge request via user interface 54 (130). Processor 50 may calculate the cumulative thermal dose to verify how much heat tissue surrounding IMD 14 has been exposed to recently (132). When processor 50 calculates the tissue temperature using transmitted power, processor 50 may calculate the cumulative thermal dose without data from IMD 14. When processor 50 calculates the tissue temperature using power measured in IMD 14 or temperatures measured at IMD 14, processor 50 may incorporate the appropriate data received from IMD 14. As described herein, the cumulative thermal dose may be calculated based upon tissue temperatures over a period of time. Since the period of time may be a rolling period of time, the cumulative thermal dose may decrease with time as rechargeable power source 18 is not being charged.

If the cumulative thermal dose is less than the thermal dose threshold ("NO" branch of block 134), processor 50 selects the high power level for charging (140). If the cumulative thermal dose is equal to or greater than the thermal dose threshold ("YES" branch of block 134), processor 50 selects the low power level for charging (136). If processor 50 is switching to a low power level from a high power level, user interface 54 may notify the user via a sound or visual indication that such change has occurred. Processor 50 then instructs charging module 58 to charge rechargeable power source 18 with the selected power level (138). In alternative examples, processor 30 may calculate the cumulative thermal dose and or select the power level for charging. In these examples, processor 50 may incorporate this information received from IMD 14 to perform at least some of the elements of FIG. 8.

If rechargeable power source 18 has not yet reached a 100 percent, or full, charge level ("NO" branch of block 142), then processor 50 continues to calculate the cumulative thermal dose (132). If rechargeable power source 18 has reached a 100 percent, or full, charge level ("YES" branch of block 142), then processor 50 may instruct charging module 58 to terminate charging (144). In other words, processor 50 may select a zero power level. Charging device 20 may subsequently notify the user of the completed recharge of rechargeable power source 18 and IMD 14 (146). This notification may be in the form of an audible alert or visual indicator provided by user interface 54. Processor 50 may also terminate charging upon request from the user.

In alternative examples, processor 50 may not charge rechargeable power source 18 when the cumulative thermal dose meets or exceeds the thermal dose threshold. Therefore, not even a low power level would be selected. The ability to charge rechargeable power source 18 at any power level after the cumulative thermal dose has exceeded the thermal dose threshold may be dependent upon how much heat is generated in IMD 14 when various power levels are used to charge rechargeable power source 18. Although a low power level may be acceptable for charging at any time in some systems and patients, other systems may be programmed to not allow any charging after the thermal dose threshold is exceeded.

Figure 9:
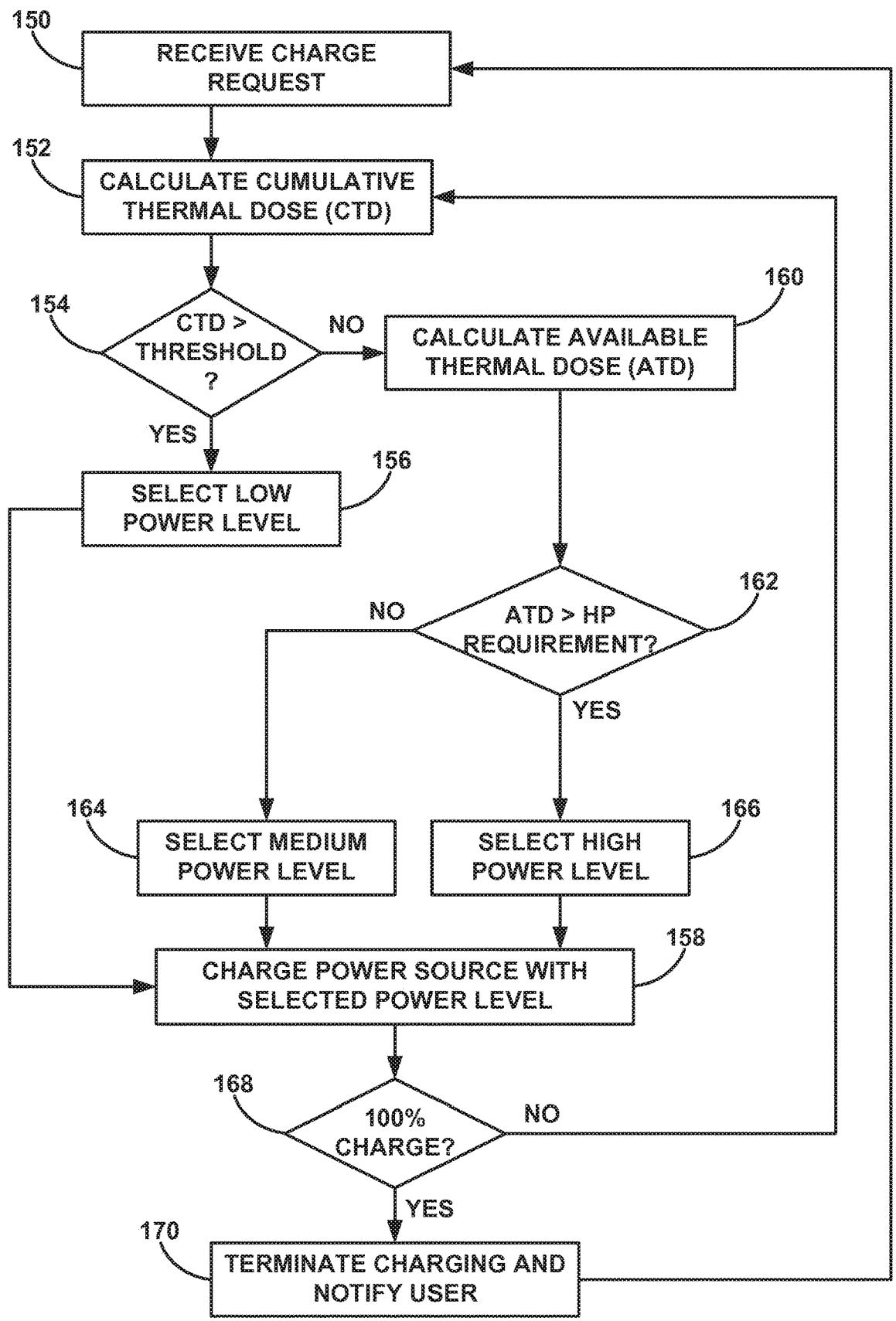
FIG. 9 is a flow diagram that illustrates an example technique for selecting a power level for charging an implantable rechargeable power source based on an available cumulative thermal dose remaining for the charging process.

FIG. 9 is a flow diagram that illustrates an example technique for selecting a power level for charging implantable rechargeable power source 18 based on an available cumulative thermal dose remaining for the charging process. The available thermal dose may allow charging power levels to be reduced prior to exceeding the thermal dose threshold. Although processor 50 of charging device 20 will be described as performing the technique of FIG. 9, the technique of FIG. 9 may instead be performed by processor 30 of IMD 14, or a combination of processors 30 and 50, in other examples.

A charging session for rechargeable power source 18 may begin when processor 50 receives a charge request via user interface 54 (150). Processor 50 may calculate the cumulative thermal dose to verify how much heat tissue surrounding IMD 14 has been exposed to recently (152). If the cumulative thermal dose is less than the thermal dose threshold ("NO" branch of block 154), processor 50 calculates the available thermal dose (160). If the available thermal dose is greater than the high power dose requirement ("YES" branch of block 162), processor 50 selects the high power level for charging (166). If the available thermal dose is less than the high power dose requirement ("NO" branch of block 162), processor 50 selects the medium power level for charging (164). The medium power level may allow IMD 14 to lower its temperature, and the lower the rate at which the cumulative thermal rate increases, while still charging rechargeable power source 18.

If the cumulative thermal dose is equal to or greater than the thermal dose threshold ("YES" branch of block 154), processor 50 selects the low power level for charging (156). If processor 50 is switching to a different power level, user interface 54 may notify the user via a sound or visual indication that such change has occurred. After the selection of the appropriate power level, processor 50 then instructs charging module 58 to charge rechargeable power source 18 with the selected power level (158). This technique for selecting power levels for charging rechargeable power source 18 and IMD 14 may allow processor 50 to limit heat radiated by IMD 14 after the thermal dose threshold has been exceeded.

If rechargeable power source 18 has not yet reached a 100 percent, or full, charge level ("NO" branch of block 168), then processor 50 continues to calculate the cumulative thermal dose (152). If rechargeable power source 18 has reached a 100 percent, or full, charge level ("YES" branch of block 168), then processor 50 may instruct charging module 58 to terminate charging and notify the user of the termination (170). This notification may be in the form of an audible alert or visual indicator provided by user interface 54. Processor 50 may also terminate charging upon request from the user.

Figure 10:
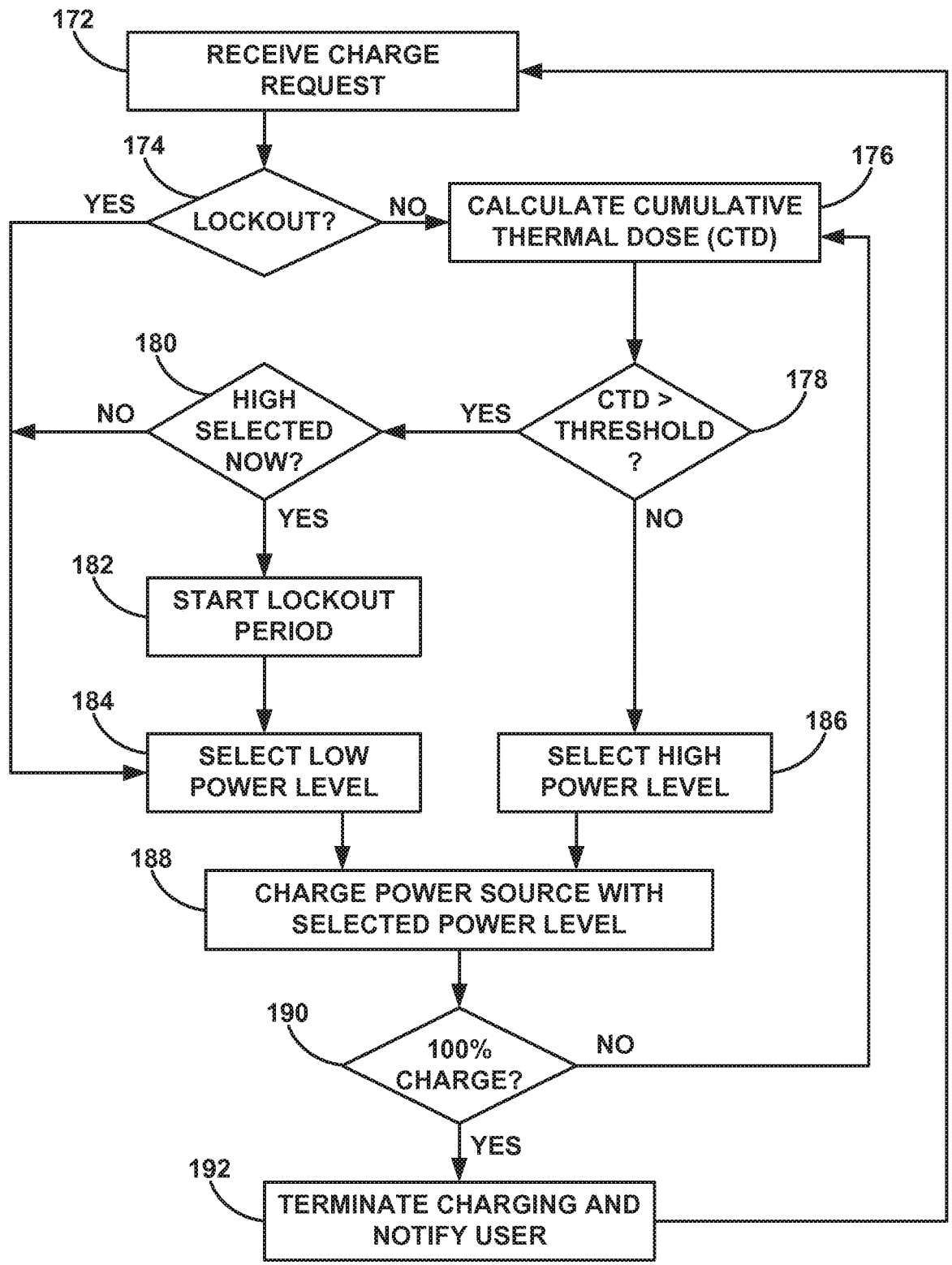
FIG. 10 is a flow diagram that illustrates an example technique for implementing a lockout period for high power level charging of a rechargeable power source.

FIG. 10 is a flow diagram that illustrates an example technique for implementing a lockout period for high power level charging of a rechargeable power source. The lockout period may prevent charging device 20 from charging IMD 14 and exposing surrounding tissue to unacceptable temperatures. Although processor 50 of charging device 20 will be described as performing the technique of FIG. 10, the technique of FIG. 10 may instead be performed by processor 30 of IMD 14, or a combination of processors 30 and 50, in other examples.

A charging session for rechargeable power source 18 may begin when processor 50 receives a charge request via user interface 54 (172). If processor 50 determines that the lockout period has not yet expired ("YES" branch of block 174), the processor 50 may select the low power level for charging (184). If processor 50 determines that the lockout period has expired ("NO" branch of block 174), then processor 50 may calculate the cumulative thermal dose to verify how much heat tissue surrounding IMD 14 has been exposed to recently (176). If the cumulative thermal dose is less than the thermal dose threshold ("NO" branch of block 178), processor 50 selects the high power level for charging (186).

If the cumulative thermal dose is equal to or greater than the thermal dose threshold ("YES" branch of block 178), processor 50 determines if the current selected power level is the high power level (180). If the high power level is currently selected ("YES" branch of block 180), processor 50 starts the lockout period (182) and selects the low power level for charging (184). If the high power level is not currently selected ("NO" branch of block 180), then processor 50 selects the low power level (184). In this manner, processor 50 begins or initiates the lockout period upon switching from the high power level. The lockout period thus prevents processor 50 from selecting the high power level again until the lockout period has expired (174). After the selection of the appropriate power level, processor 50 then instructs charging module 58 to charge rechargeable power source 18 with the selected power level (188).

If rechargeable power source 18 has not yet reached a 100 percent, or full, charge level ("NO" branch of block 190), then processor 50 continues to calculate the cumulative thermal dose (176). If rechargeable power source 18 has reached a 100 percent, or full, charge level ("YES" branch of block 168), then processor 50 may instruct charging module 58 to terminate charging and notify the user of the termination (192). This notification may be in the form of an audible alert or visual indicator provided by user interface 54. Processor 50 may also terminate charging upon request from the user.

In the example of FIG. 10, the lockout period may be a predetermined period regardless of the amount of time the high power level was used to charge rechargeable power source 18 or the cumulative thermal dose. In some examples, processor may calculate the lockout period duration when the lockout period is started. The lockout period may be based on the duration the high power level was used to charge rechargeable power source 18, e.g., longer high power level charging would result in a longer lockout period. In other examples, the lockout period may reflect the cumulative thermal dose such that the lockout period may expire upon the cumulative thermal dose dropping below a threshold. In this manner, processor 50 may calculate the cumulative thermal dose prior to determining if the lockout period has expired. In any case, the lockout period may be implemented by charging device 20 or IMD 14 to prevent excessive IMD 14 temperatures from higher power levels, or higher charging rates, during a recharge session.

According to the techniques and devices described herein, a cumulative thermal dose may be calculated as feedback for the selection of a power level used to charge a rechargeable power source in an IMD. The power level may be reduced upon the cumulative thermal dose exceeding a threshold to limit the risk of undesirable and uncomfortable higher 1 MB temperatures during recharging. The cumulative thermal dose may also allow for real-time feedback that allows a charging device to charging the rechargeable power source at high rates in a "boost mode" and lower the charging rate before the temperature may be damaging to tissue. In this manner, the charging device or 1 MB may balance the desire for fast charging rates with patient safety without estimations used in open-loop charging techniques.

This disclosure is primary directed to wireless transfer of energy between two coils (e.g., inductive coupling). However, one or more aspects of this disclosure may also be applicable to energy transfer involving a physical connection between a charging device and a rechargeable power supply. For example, aspects of this disclosure may be applicable to charging the power supply of an 1 MB by inserting a needle coupled to an external charging device through the skin and into a port of the IMD. Although physical connections for energy transfer may not introduce heat losses due to energy transfer between wireless coils, heat may still be generated and lost to the patient from components within the 1 MB (e.g., the battery being charged and circuits involved in the recharging of the power supply).

Various examples have been described. These and other examples are within the scope of the following claims.

The invention claimed is:

1. A system comprising:
   processing circuitry configured to:
      calculate an estimated cumulative thermal dose delivered to a patient during charging of a rechargeable power source of an implantable medical device over a period of time;
      select, based on the estimated cumulative thermal dose, a power level for subsequent charging of the rechargeable power source; and control a charging module to charge the rechargeable power source according to the selected power level.

2. The system of claim 1, wherein to control the charging module to charge the rechargeable power source, the processing circuitry is configured to:
cause the charging module to generate a first electrical current in a primary coil based on the selected power level; and
cause the charging module to induce an electrical current in an implanted secondary coil associated with the rechargeable power source.

3. The system of claim 1, wherein the period of time is one of selected from between approximately one hour and forty-eight hours or a single recharge session.

4. The device of claim 1, wherein to select the power level, the processing circuitry is configured to:
select a high power level when the estimated cumulative thermal dose has not exceeded a thermal dose threshold; and
select a low power level when the estimated cumulative thermal dose has exceeded the thermal dose threshold.

5. The system of claim 1, wherein to select the power level, the processing circuitry is configured to:
calculate an available thermal dose by subtracting the estimated cumulative thermal dose from a thermal dose threshold;
select a high power level when the available thermal dose is greater than a high power dose requirement; and
select a low power level when the available thermal dose is less than the high power dose requirement.

6. The system of claim 1, wherein the processing circuitry is further configured to:
initiate a lockout period after controlling the charging module to charge the rechargeable power source with a high power level; and
control the charging module to prevent selection of the high power level during the lockout period and allow selection of a low power level during the lockout period, wherein a duration of the lockout period is based on a previous charging time with the high power level.

7. The system of claim 1, wherein to calculate the estimated cumulative thermal dose, the processing circuitry is configured to calculate an integral of a tissue temperature over the period of time.

8. The system of claim 7, wherein the processing circuitry is further configured to receive a signal indicative of the tissue temperature adjacent to the rechargeable power source.

9. The system of claim 7, wherein the processing circuitry is further configured to calculate the tissue temperature based on a tissue model and power transmitted to the rechargeable power source over the period of time.

10. The system of claim 1, wherein one of the implantable medical device or an external charging device comprises the processing circuitry.

11. The system of claim 1, wherein the implantable medical device comprises a first portion of the processing circuitry, and wherein an external charging device comprises a second portion of the processing circuitry.

12. A method comprising:
calculating, by processing circuitry, an estimated cumulative thermal dose delivered to a patient during charging of a rechargeable power source of an implantable medical device over a period of time;
selecting, by the processing circuitry based on the estimated cumulative thermal dose, a power level for subsequent charging of the rechargeable power source; and
controlling, by the processing circuitry, a charging module to charge the rechargeable power source according to the selected power level.

13. The method of claim 12, wherein controlling the charging module to charge the rechargeable power source comprises:
causing the charging module to generate a first electrical current in a primary coil based on the selected power level; and
causing the charging module to induce an electrical current in an implanted secondary coil associated with the rechargeable power source.

14. The method of claim 12, wherein selecting the power level comprises:
selecting a high power level when the estimated cumulative thermal dose has not exceeded a thermal dose threshold; and
selecting a low power level when the estimated cumulative thermal dose has exceeded the thermal dose threshold.

15. The method of claim 12, wherein selecting the power level comprises:
calculating an available thermal dose by subtracting the estimated cumulative thermal dose from a thermal dose threshold;
selecting a high power level when the available thermal dose is greater than a high power dose requirement; and
selecting a low power level when the available thermal dose is less than the high power dose requirement.

16. The method of claim 12, wherein method further comprises:
initiating, by the processing circuitry, a lockout period after controlling the charging module to charge the rechargeable power source with a high power level; and
controlling, by the processing circuitry, the charging module to prevent selection of the high power level during the lockout period and allow selection of a low power level during the lockout period, wherein a duration of the lockout period is based on a previous charging time with the high power level.

17. The method of claim 12, wherein calculating the estimated cumulative thermal comprises calculating an integral of a tissue temperature over the period of time.

18. The method of claim 17, wherein the method further comprises receiving, by the processing circuitry, a signal indicative of the tissue temperature adjacent to the rechargeable power source.

19. The method of claim 17, wherein the method further comprises calculating the tissue temperature based on a tissue model and power transmitted to the rechargeable power source over the period of time.

20. A computer-readable storage medium comprising instructions that cause processing circuitry to:
calculate an estimated cumulative thermal dose delivered to a patient during charging of a rechargeable power source of an implantable medical device over a period of time;
select, based on the estimated cumulative thermal dose, a power level for subsequent charging of the rechargeable power source; and control a charging module to charge the rechargeable power source according to the selected power level.

\* \* \* \* \*